United States Patent [19]
Coe

[11] Patent Number: 5,552,025
[45] Date of Patent: Sep. 3, 1996

[54] SENSORS

[75] Inventor: David E. Coe, St. Neots, England

[73] Assignee: ABB Kent-Taylor Limited, Bedfordshire, England

[21] Appl. No.: 230,065

[22] Filed: Apr. 20, 1994

[30] Foreign Application Priority Data

Apr. 22, 1993 [GB] United Kingdom .................. 9308305

[51] Int. Cl.$^6$ .................................................. G01N 27/26
[52] U.S. Cl. ..................... 205/785.5; 204/421; 204/424; 204/426; 204/427
[58] Field of Search .................................... 204/421, 426, 204/427, 424, 153.19, 153.16, 290 R; 429/33, 193

[56] References Cited

U.S. PATENT DOCUMENTS

| | | | |
|---|---|---|---|
| 4,276,202 | 6/1981 | Schmidberger et al. | 204/290 R |
| 4,388,155 | 6/1983 | Chamberland et al. | 204/426 |
| 4,526,844 | 7/1985 | Yoldas et al. | 429/33 |
| 4,715,944 | 12/1987 | Yanagida et al. | 204/426 |
| 4,789,454 | 12/1988 | Badwal et al. | 204/421 |
| 5,192,404 | 3/1993 | Fray et al. | 204/153.19 |

*Primary Examiner*—Bruce F. Bell
*Attorney, Agent, or Firm*—Hodgson, Russ, Andrews, Woods & Goodyear LLP

[57] ABSTRACT

A sensor for measuring sulphur dioxide in flue gases comprises a sensing electrolyte of doped β-alumina or doped NASICON. The dopant serves to increase conductivity at grain boundaries in the sensing element or at the electrode interface, thereby to increase the rate of depolarisation. Preferred dopants are copper silver and nickel.

28 Claims, 22 Drawing Sheets

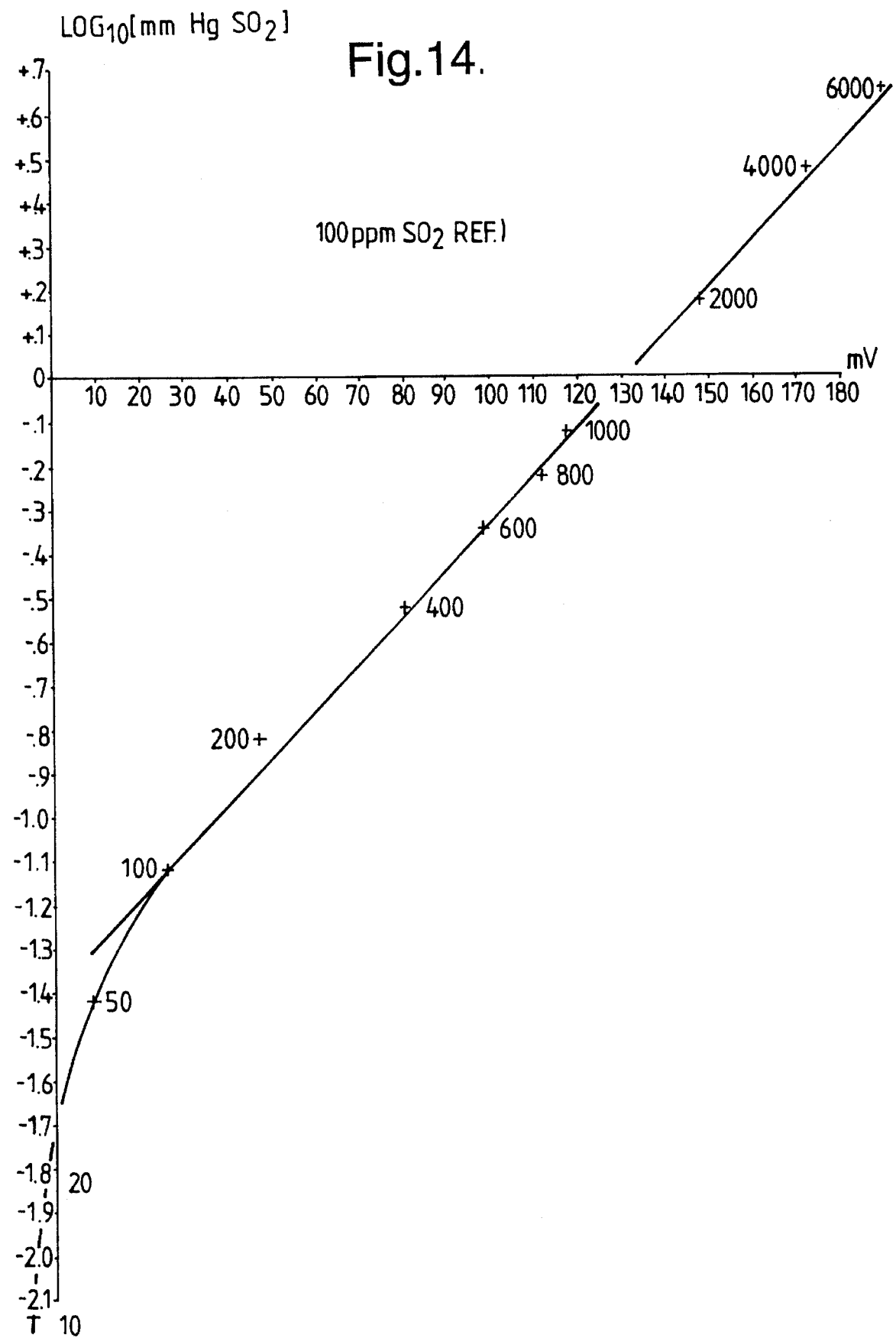

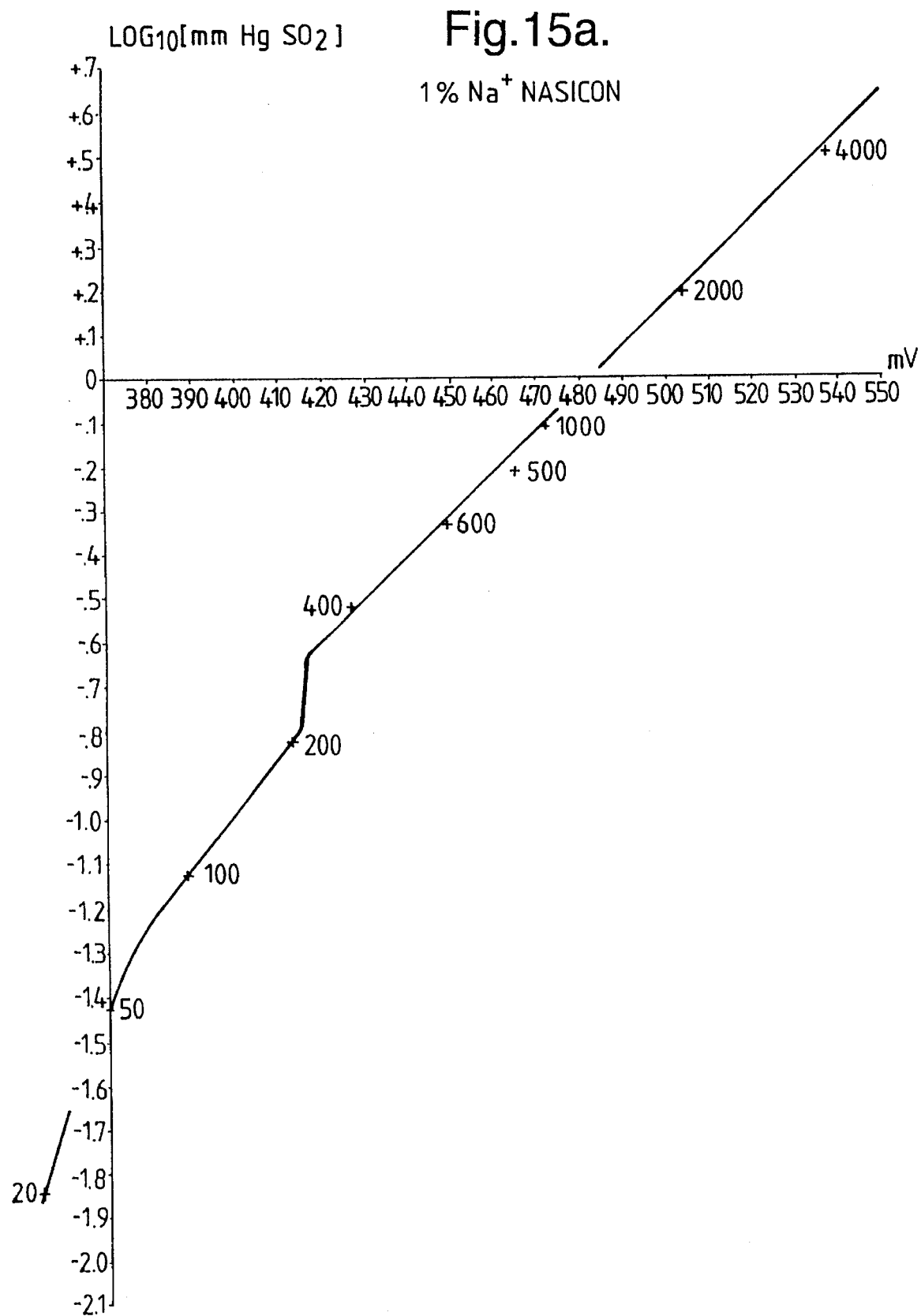

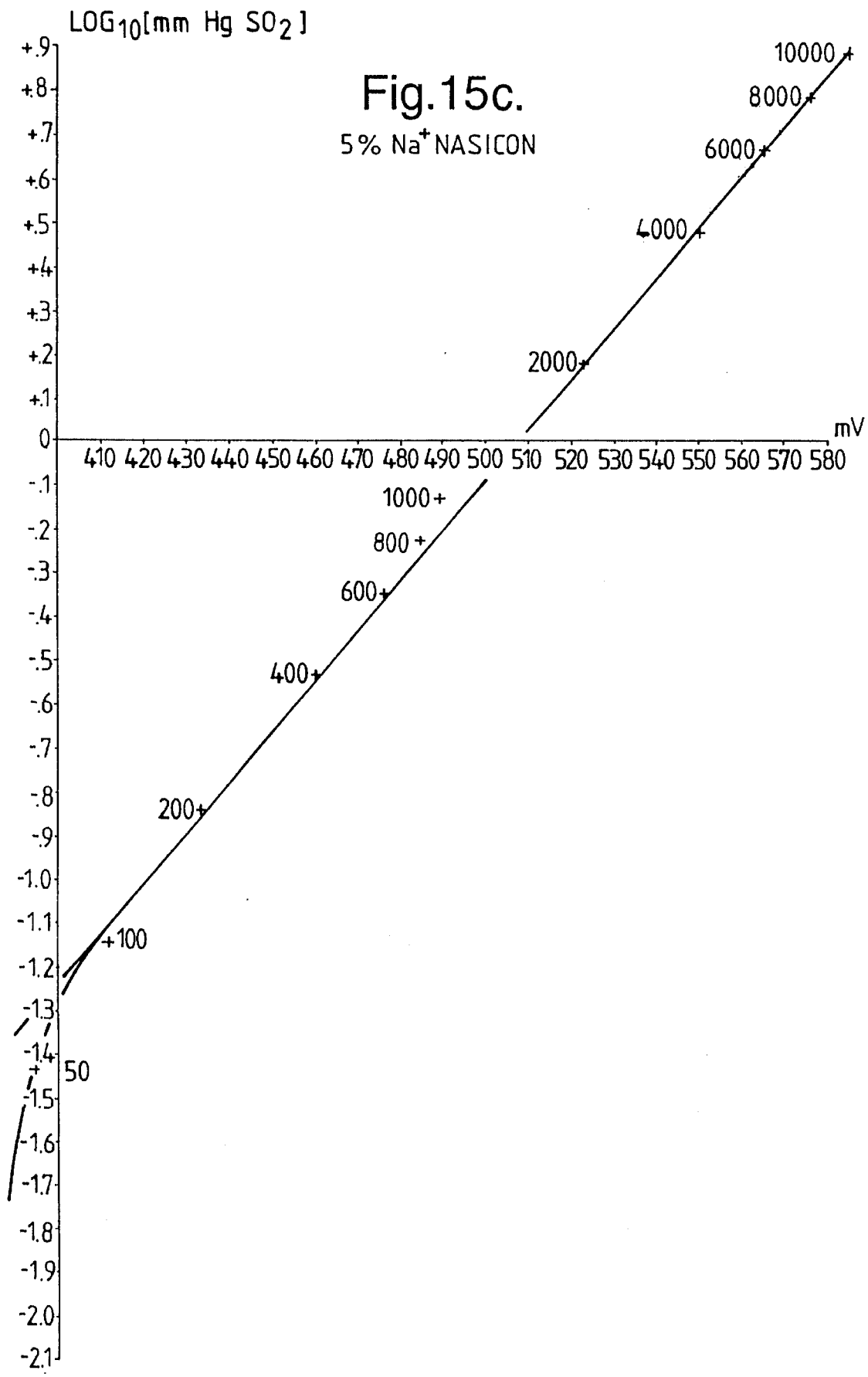

10% Na⁺ NASICON

SENSORS

The invention relates to improved sensors for measuring sulphur oxides in gases, particularly sulphur dioxide, probes incorporating the sensors and methods of measuring sulphur oxides in gases, particularly sulphur dioxide.

The need to sense the presence of sulphur dioxide in gases arises in a wide variety of applications, in particular in the monitoring of boiler flue gases. This application is of increased importance to electricity generating stations which are now obliged to control their levels of emission.

Ceramic electrolytes have been proposed for use in such sensors. Examples of such electrolytes have been described in *J. Electrochem. Soc* 124 1579 (1977), *J. Electrochem. Soc* 124 1584 (1977), *J. Electrochem. Soc* 126 1842 (1979) and *Solid State Ionics* 17 281 (1985). Particularly preferred ceramic electrolytes are potassium sulphate, β-alumina and NASICON. NASICON is a range of materials, the parent member of which is $Na_3Zr_2Si_2PO_{12}$.

The sensing element is usually in the form of a tube or disc which is mounted to expose one side to the gas to be measured. The other side is exposed to a reference gas having a known partial pressure of oxygen and sulphur dioxide. Electrodes of porous electron conductive ceramic or metal are connected to the two sides of the sensing element so that the electrical potential which will develop between the electrodes can be measured.

Alternatively, the reference may be a solid or liquid with a metal electrode such that a fixed reference potential is set up between the solid or liquid and the metal electrode.

The electrical potential, E, that is developed between the electrodes is in accordance with the Nernst equation.

$$E = E^0 + \frac{RT}{nF} \ln \frac{Po_2^{meas}}{Po_2^{ref}} + \frac{RT}{nF} \ln \frac{Pso_2^{meas}}{Pso_2^{ref}}$$

where RT/nF is the Nernst constant, $E^0$ is the cell offset potential, $Po_2$meas is the partial pressure of oxygen in the measured gas, $Po_2$ref is the partial pressure of oxygen in the reference gas, $Pso_2$meas is the partial pressure of sulphur dioxide in the measured gas and $Pso_2$ref is the partial pressure of sulphur dioxide in the reference gas. Thus the partial pressure of the sulphur dioxide in the measured gas can be obtained and thereby its concentration ascertained.

Known sensors employing ceramic electrolytes exhibit certain disadvantages when applied to industrial applications. For example, an alkali metal sulphate is too fragile to produce a reliable sensor in typical industrial applications.

The β-alumina used in known sensors may include lithium or magnesium ions to stabilize the β" phase. The presence of the lithium or magnesium, which acts in the bulk material, improves the mechanical strength of the β-alumina. However, this grade of β-alumina exhibits significant hysteresis in sulphur dioxide response and the sensor therefore cannot produce the level of accuracy generally desired in industrial applications.

In an ideal sensor, a Nernstian plot of measurements taken on increasing and decreasing concentrations of sulphur dioxide would comprise of two lines, the slopes of which would coincide. As illustrated in FIG. 1, the Nernstian slope for increasing concentrations of sulphur dioxide are often close to theoretical. However, for decreasing concentration the Nernstian slope is significantly less than theoretical.

It can be seen from FIG. 1 that the difference between the two slopes is of the order of a few tens of millivolts. While this may appear to be a relatively small difference, in sensor applications this may represent a measurement error of 20% or more.

Known sensors incorporating reference half cells require a reference gas having known partial pressures of oxygen and sulphur dioxide which must remain constant throughout the operation of the sensor. As the reference gas is usually supplied from a gas cylinder, frequent replenishment may be required, increasing the cost of using the sensor. In addition, partial pressures may differ between cylinders.

It has been suggested that zirconia/oxygen reference electrodes may be suitable, *J. Electrochem. Soc* 128 371 (1981). However, these can be unstable and give sluggish responses when used in combination with alkali metal ion conducting electrolytes.

An alternative suggestion is the use of molten sodium as a reference or, as in *Trans. Jap. Inst. Metals* 25 504 (1984), a sodium-gold alloy may be used. However, both these reference electrodes require an inert atmosphere which increases the difficulties of using them in an industrial situation. In addition, molten sodium is a potential safety hazard.

It is a further disadvantage of certain known sensors used for measuring boiler flue gases, that—before measurement—the hot flue gases must be chilled.

We have now found an alternative sensing electrolyte which is suitable for use in industrial applications.

In accordance with one aspect of the present invention, there, is provided a sensor for measuring sulphur dioxide or sulphur trioxide in gas comprising a sensing element capable of being exposed to the gas to be measured and electrode means for use in measuring an electrochemically developed potential, and in which the sensing element comprises an electrolyte of doped β-alumina or doped NASICON.

The NASICON used may be any of the range of materials, the parent member of which is $Na_3Zr_2Si_2PO_4$, and which has the required activity.

The presence of the dopant ions in the electrolyte leads to an improvement in the polarization effects and thereby reduces hysteresis in the response to the presence of sulphur dioxide. Thus, a sensor of improved accuracy and sensitivity is obtained. Other benefits obtained by the use of a sensor in accordance with the present invention include a reduction in the drift in response with time and an increased stability of response output.

By β-alumina, we mean β/β" alumina. Lithium or magnesium ions may be included to stabilize the β" phase.

Without wishing to be bound by any particular theory, it is believed that, in the present invention hysteresis is reduced by increasing the rate of depolarization at the grain boundaries, by increasing the rate of depolarization at the electrode/electrolyte interface or by increasing both rates of depolarization.

The rate of depolarization at the grain boundaries within the electrolyte may be increased by improving conductivity. This may be achieved by distorting the structure of the molecules by the insertion of an ion. Where the electrolyte is β-alumina this may be achieved by the use of a dopant which replaces aluminum in the alumina. In this case, it is important that the dopant has an ionic radius different from that of aluminium. Alternatively the structure of β-alumina may be distorted by the presence of a dopant in the tetrahedral sites.

Similarly, where the electrolyte is a NASICON compound, the structure may be distorted by replacing Zr or Si with dopant having a differing ionic radius.

Suitable dopant ions are those which reduce polarization at the electrode/electrolyte interface, at the grain boundaries of the β-alumina or NASICON or at both. Examples of suitable dopants include silver, copper, nickel, uranium, chromium, manganese, cobalt, thallium, vanadium, cerium, palladium, iron, zinc, lead, tin, mercury, cadmium, europium or rhodium, with silver, copper, nickel, uranium, chromium, manganese, cobalt and vanadium being particularly preferred. The dopants are preferably present in an amount of from 0.1 to 30 mol %, more preferably 0.1 to 10mol %.

As two effects may be required, that is the reduction of polarisation at the electrode/electrolyte interface and the reduction of polarization at the grain boundaries, it is possible that the electrolyte may be doped with two dopants, the first having optimal effect at the electrode/electrolyte interface and the second having optimal effect at the grain boundaries.

In addition to the effect on polarization the redox potential of the dopant is also important. In particular, the dopant used to decrease polarization at the electrode/electrolyte interface should be stable and close to that of $SO_2$. Thus, particularly suitable dopants for this purpose include manganese, thallium, palladium, vanadium, uranium, chromium, cerium, rhodium and lead.

It is an object of a further aspect of this invention to remove the need for a reference level of sulphur dioxide.

Accordingly, the present invention consists in another aspect of the present invention in a sulphur oxide sensor comprising a solid state sensing electrolyte responsive to a sulphur oxide and to oxygen and a solid state reference electrolyte in electrochemical association with the sensing electrolyte such that the electrochemical response of the sensor is representative of the sulphur oxide level for a known level of oxygen, the reference electrolyte being selected from the group consisting of NASICON, doped NASICON, mixed phase alumina and doped alumina.

Thus the need for cylinders of sulphur dioxide and oxygen of known concentration is obviated.

The reference electrolyte may be $(\alpha+\beta)$ alumina or it may be NASICON doped with sodium, the sodium may be present in an amount of 33 mol %, more preferably 10 mol %, or less. Sodium present in an amount of 2 mol % is particularly preferred. The quoted concentration of sodium is a sodium excess over that already present in the NASICON structure.

The electrodes, which may be the same or different, may comprise a noble metal or an electron conducting ceramic. A suitable metal is platinum and a suitable ceramic is perovskite-lanthanum nickelate ($LaNiO_3$).

According to a further aspect of the present invention, there is provided a probe for measuring a sulphur oxide in gas comprising a sensor as hereinbefore defined and an oxygen compensator associated with the sensing element and the reference electrolyte such that a measure of the sulphur oxide level is obtained which is independent of the oxygen level in the gas.

Thus, where the sensing element responds to both—say—sulphur dioxide and oxygen, the oxygen response, known from the compensator, can be subtracted. This results in an accurate measure of sulphur dioxide.

Many known oxygen sensors would be suitable, however a zirconia oxygen sensor is particularly suitable.

The sensor and the oxygen compensator may be located in the same housing thereby reducing production costs and producing a single unit which is readily installed. The probe may include at least one heating means, which may be common.

According to a further aspect of the present invention, there is provided a method of measuring a sulphur oxide in gas, comprising the steps of exposing to the gas a sensing electrolyte of doped β-alumina or doped NASICON and detecting an electrochemically developed potential.

It is an object of a still further aspect of the present invention to obviate the need for a separate oxygen determination.

Accordingly, the aspect invention consists in a further aspect in a sulphur dioxide probe comprising a first sensing electrolyte responsive to sulphur dioxide and oxygen and a second sensing electrolyte in electrochemical association with the first and responsive to oxygen, wherein the overall response to the probe is indicative of sulphur dioxide level substantially independent of oxygen level.

The invention is now described by way of example with reference to the accompanying drawings in which:

FIG. 14 is a plot showing response of undoped β-alumina using as reference half cell 100 ppm sulphur dioxide in air;

Figure 16:
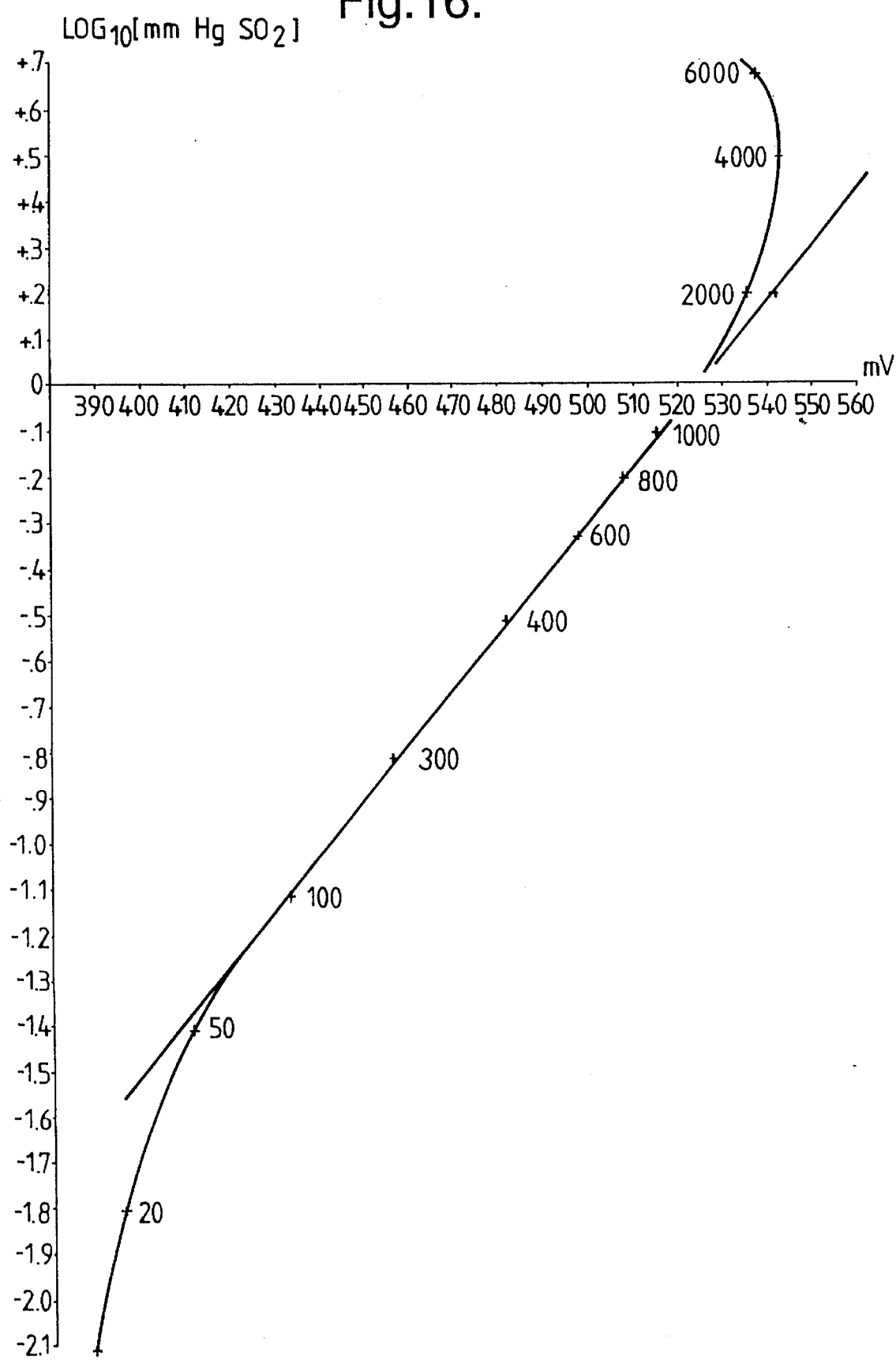
Figure 17:
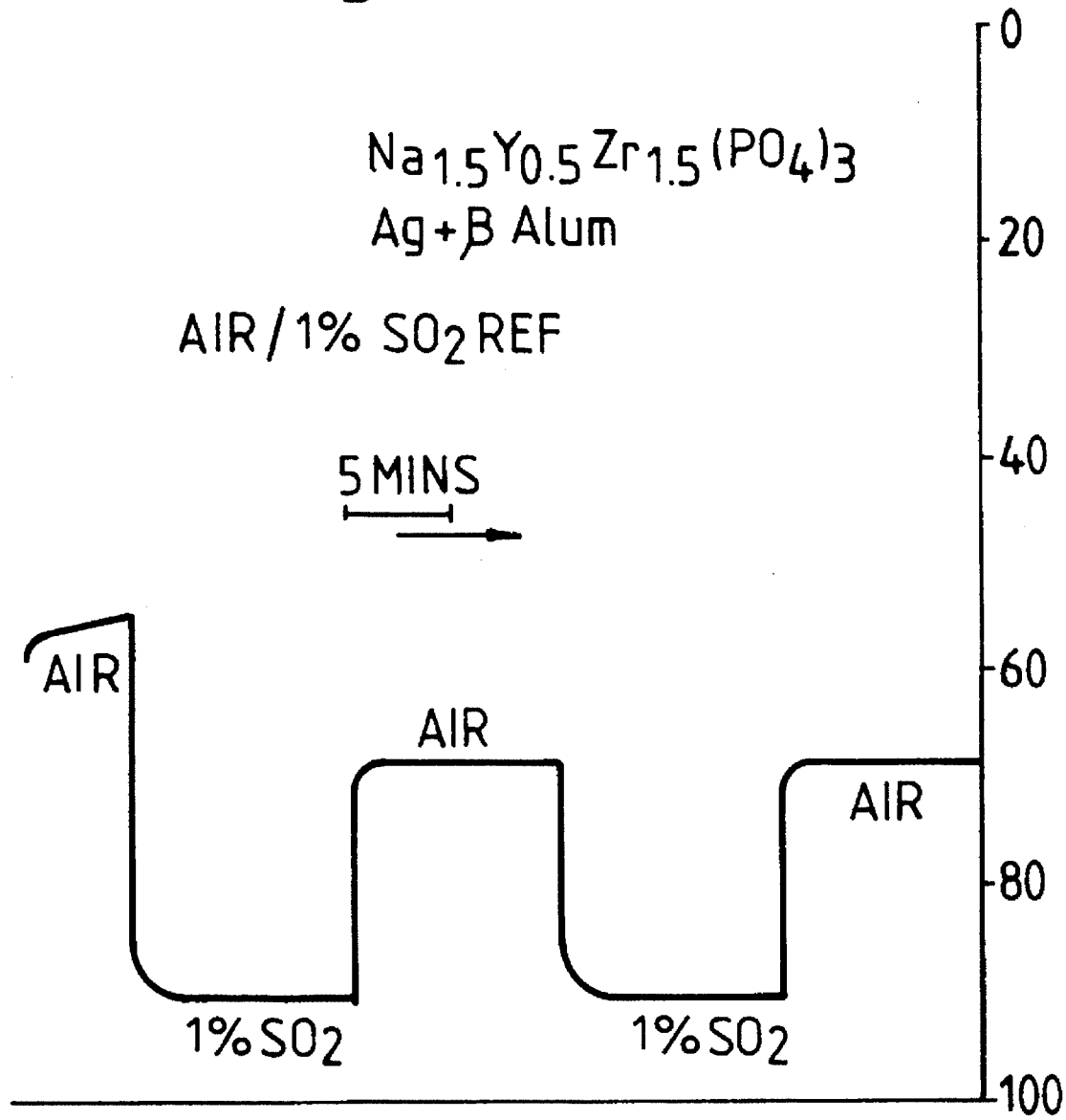
Figure 18:
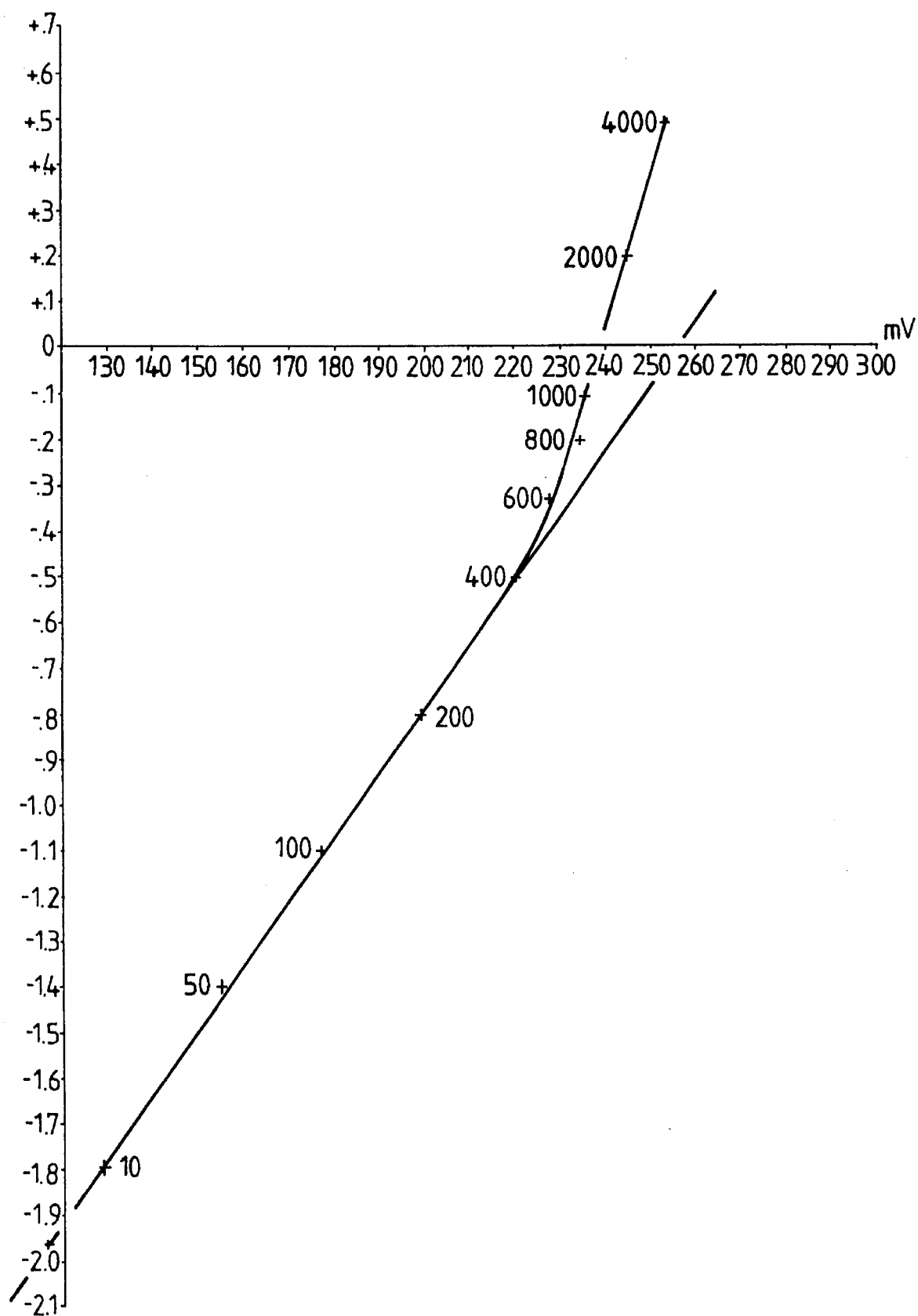

FIGS. 15a–d are plots illustrating response for NASICON/air references;

FIG. 16 is a plot illustrating the response for 0% $Na^+$ NASICON/air reference;

FIG. 17 is a plot of response of $Na_3YZr_3(PO4)_6$/air reference to 1% /0% $SO^2$ step change; and FIG. 18 is a plot illustrating response for $(x+\beta)$ phase β-alumina/air reference.

Figure 2:
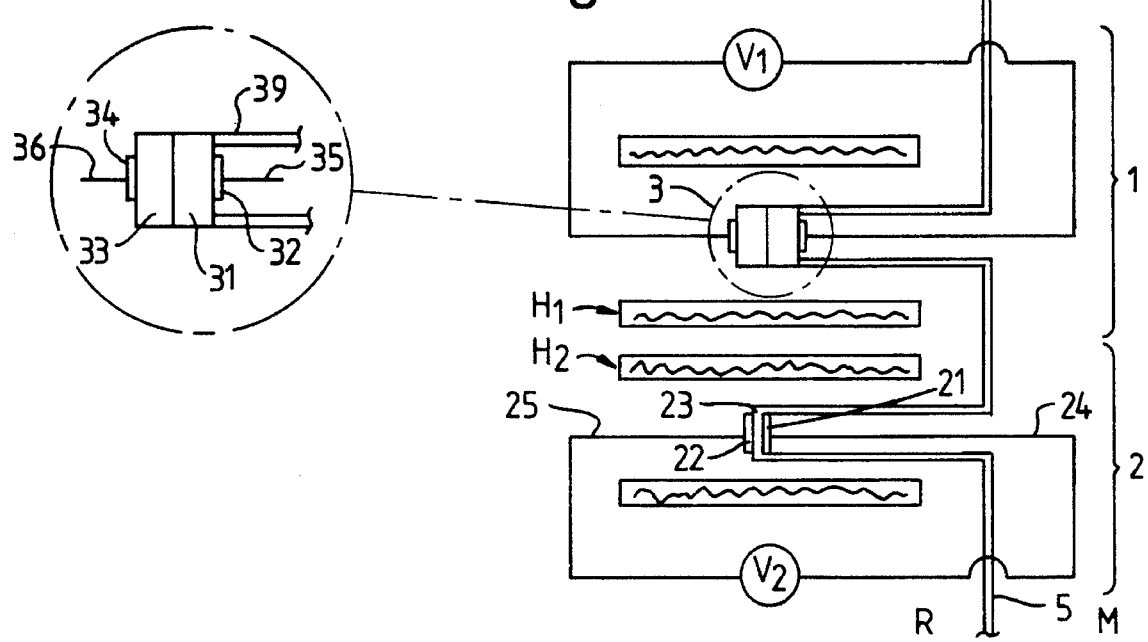
FIG. 2 is a schematic drawing of a probe according to the invention with an exploded schematic drawing of a sensor including a reference element.

Referring to FIG. 2, the probe comprises a sulphur dioxide sensor (1), an oxygen compensator (2) and a partition (5) to separate the measured gas from the reference gas. Thus components on side M of the partition are exposed to the gas, the sulphur dioxide content of which is to be measured and components on side R of the partition are exposed to the reference gas.

The sensor for measuring sulphur dioxide (1) comprises a sensing electrolyte (31) located in an insulating tube (39), which may be of alumina, and a sensing electrode (32) attached to the electrolyte. The electrode may be a porous platinum electrode. Where a reference element is to be used, the sensor (1) will additionally include a reference electrolyte (33) and an electrode (34) to form a reference half cell. Where a reference element is not to be used, the electrode (34) will be connected to the sensing electrolyte (31) on the opposing face to that bearing electrode (32). Wires (35 and 36) are connected to the electrodes (32 and 34) such that the voltage $V_1$ can be measured. $V_1$ will be dependant on the concentration of sulphur dioxide and oxygen.

The purpose of the reference half cell is to provide a counter electrode of stable potential for use in combination with the sensing half cell. It should preferably have an acceptably low drift in potential with time, have a potential unaffected by the potential changes of the sensing half cell, be electrochemically compatible with the sensing half cell and compatible with the conditions under which the sensing system is to be used.

One suitable reference half cell consists of a porous platinum electrode on the opposite face of the β-alumina disc to the sensing electrode but held in contact with a sulphur dioxide/oxygen mixture of constant composition. This is the first choice for laboratory test purposes as it reduces the number of components capable of giving problems and errors as there are no junction potentials, and there is full electrochemical compatibility.

However, this system is not very practical for a commercial sensor due to the need for a continuous supply of the reference gas mixture which is both expensive and a source of pollution. It has been shown experimentally that neither the β-alumina developed for sulphur dioxide sensing nor the grades used for sodium-sulphur batteries generate a sufficiently stable reference potential when in contact with air alone.

Liquid electrolytes are unsuitable as it is highly desirable in the envisaged applications that the probe should be capable of installation in any orientation.

What is required is a solid state reference half cell capable of setting up a stable reference potential when in contact with air without any other gaseous components. For electrochemical compatibility with the β-alumina sensing half cell it should ideally also be an alkali metal ion super-ionic conductor to avoid serious junction potentials at the interface of the two electrolytes. It should also be capable of operating in the region of 700° C.

These criteria are met by both the NASICON range of materials and β-alumina materials of low sodium ion concentration such that the material is mixed α+β phase. The NASICON materials gave the best results of the two.

The parent member of the NASICON range of materials has the composition $Na_3Zr_2Si_2PO_{12}$. To optimise the reference potential of the NASICON the sodium ion concentration is adjusted either by adding sodium oxide into the structure or by substituting all or part of the zirconium and/or silicon with different valent ions and adjusting the sodium ion content to balance charges. The first method may give a mixed phase material while the second gives a single phase material preserving the NASICON structure. Particularly suitable combinations of sensing and reference electrolytes are set out in Table 1, overleaf.

TABLE 1

| REFERENCE ELECTROLYTES | SENSING ELECTROLYTES |
| --- | --- |
| NASICON + 2% $Na^+$ | β-alumina + 2% $Cu^{22+}$ |
| NASICON + 2% $Na^+$ | β-alumina + 2% $Ag^+$ |
| NASICON + 2% $Na^+$ | β-alumina + 2% $Ni^{2+}$ |
| NASICON + 2% $Na^+$ | β-alumina + ½% $Cu^{2+}$ |
| NASICON + 2% $Na^+$ | β-alumina + 2% $Ag^+$ |
| NASICON + 2% $Na^+$ | NASICON + 2% $Ni^{2+}$ |
| NASICON + 2% $Na^+$ | β-alumina + dopant |
| (α + β) alumina | β-alumina + dopant |

Figure 3:
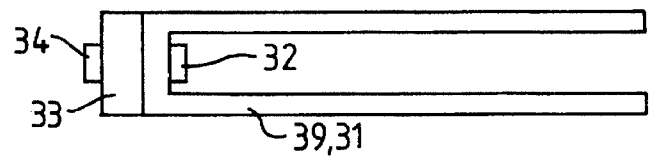
FIG. 3 is a schematic drawing of an alternative arrangement of the sensor.

An alternative arrangement for the sensor (1) is shown in FIG. 3. In this arrangement the tube and the sensing electrolyte are combined into a closed end tube.

As shown in FIG. 2, the probe may include an oxygen compensator (2) in the form of a zirconia oxygen sensor. Electrodes (21 and 22) are attached to opposing faces of the zirconia electrolyte (23). Wires (24 and 25) are connected to the electrodes (21 and 22) such that voltage $V_2$ can be measured.

$V_2$ will be dependant on the concentration of oxygen in the gas.

The probe may include thermostatic or astatic heaters $H_1$ and $H_2$ to regulate the temperature of the sensor (1) and the compensator (2). It will be appreciated that a single heater may be used or a heater of a type other than a thermostatic heater may be used.

In addition, it will be appreciated that the relative orientation of the sensor (1) and compensator (2) may differ and that they may even be located in separate housings.

Figure 4:
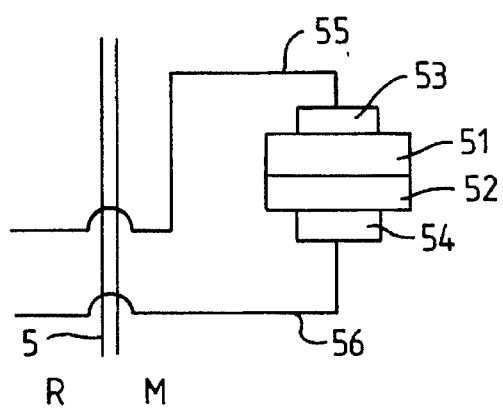
FIG. 4 is a schematic drawing of a self-compensating probe in accordance with the invention.

FIG. 4 illustrates an alternative arrangement for a sensor according to the present invention in which the compensator and the reference half cell have been combined.

The probe comprises a sensor having a sensing electrolyte (51) with an electrode (53) attached thereto and a combined reference element and oxygen compensator (52) with an electrode (54) attached thereto. Wires (55 and 56) enable the electrical potential between the electrodes (53 and 54) to be measured.

The reference element and the sensor element are both on the same side M of the partition (5) and are therefore exposed to the gas to be measured. The need for a reference gas is thereby obviated. If the sensing electrolyte (51) and the reference electrolyte (52) are selected such that they respond equally well to oxygen then the overall response to oxygen will be zero. Zirconia is particularly suitable for use in the reference half cell (52) since it is insensitive to sulphur dioxide. Thus the overall cell response will be due to the presence of sulphur dioxide in the measured gas.

The present invention can be illustrated by the following examples:

EXAMPLE 1

Two β-alumina samples were prepared. The first was doped with 2 mole % silver and the second was doped with ½% copper. The samples, having porous platinum electrodes on each face were exposed to gases having a variety of $SO_2$ concentrations in air. The $SO_2$ concentration varied from 10 ppm to 8,000 ppm.

The voltage across the β-alumina was measured and a plot of log of concentration of $SO_2$ against mV, a Nernstian plot, was produced.

Figure 1:
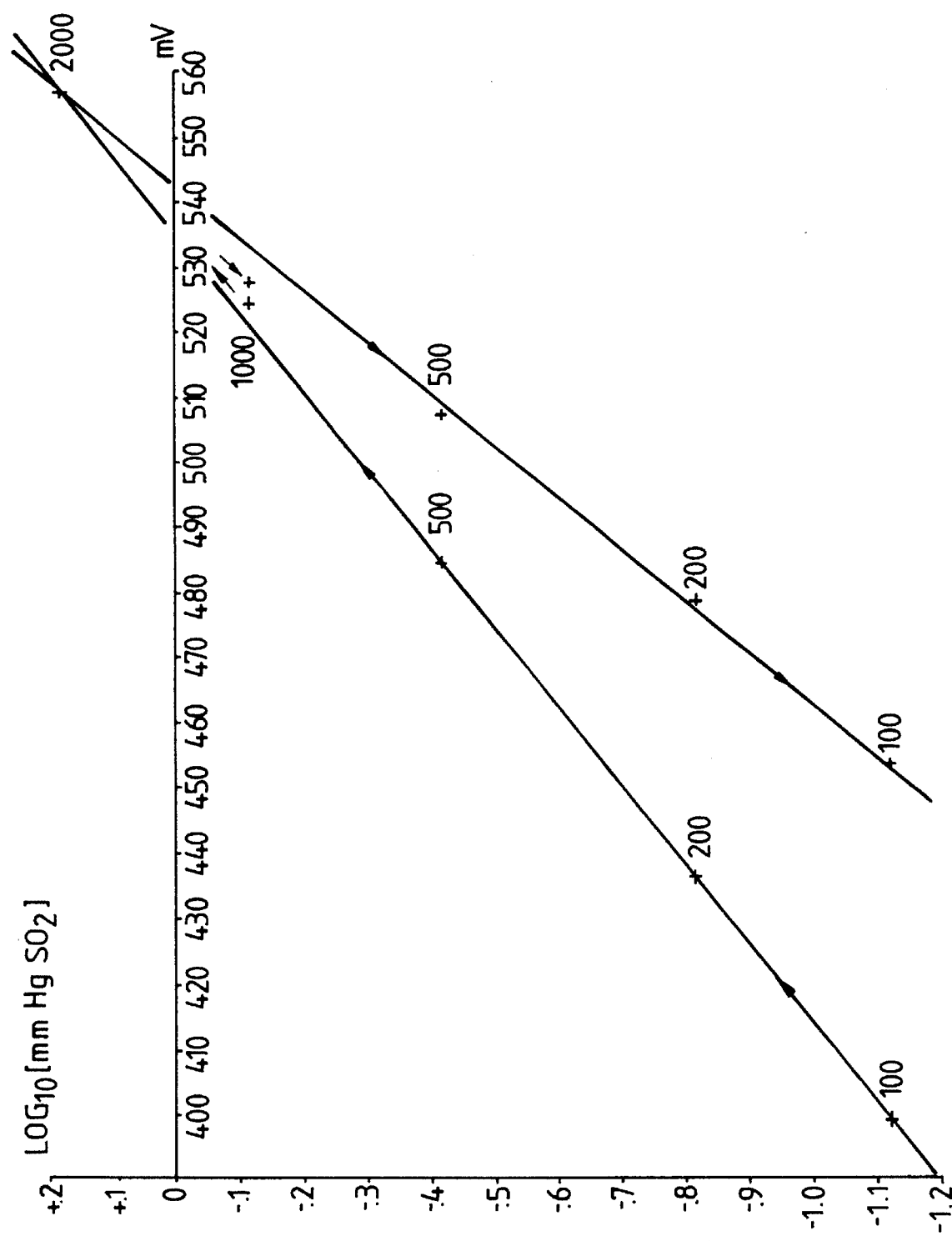
FIG. 1 is a Nernstian plot of sulphur dioxide response for undoped β-alumina.
Figure 5:
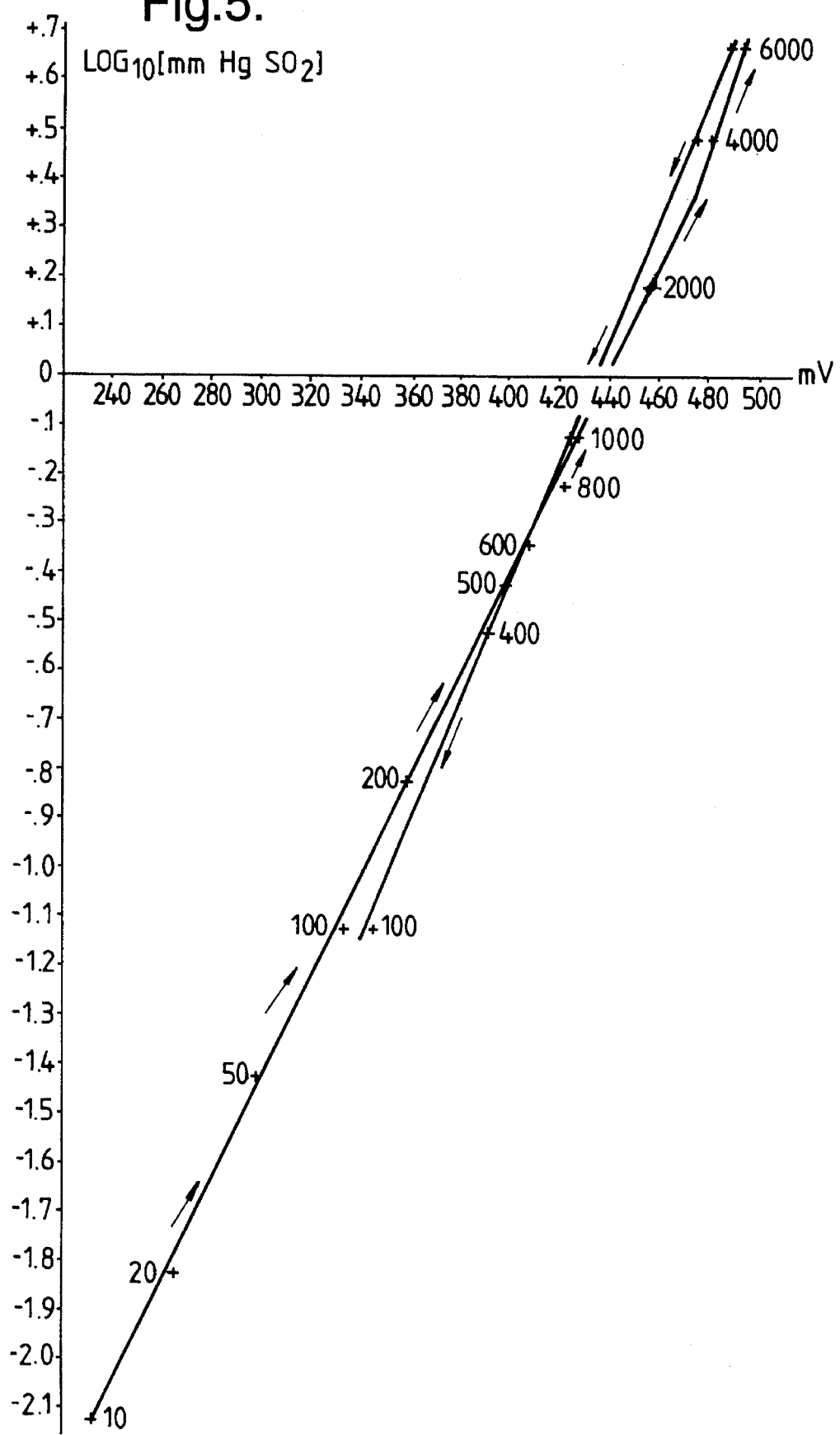
FIG. 5 is a Nernstian plot of sulphur dioxide response for 2 mole % silver doped β-alumina.
Figure 6:
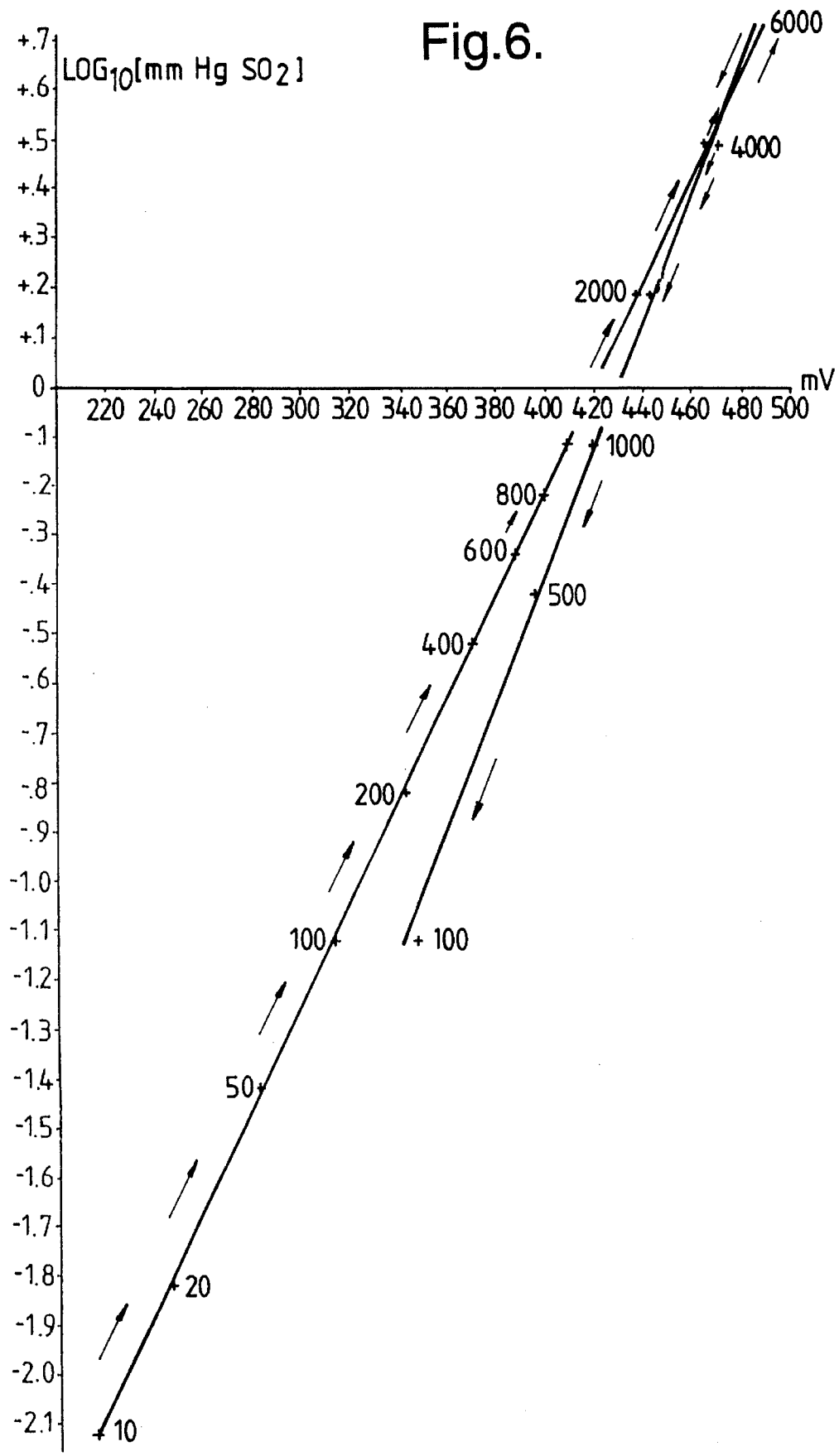
FIG. 6 is a Nernstian plot of sulphur dioxide response for ½ mole % copper doped β-alumina.

The Nernstian plots of response to a range of $SO_2$ concentrations are shown in FIG. 5 for 2 mole % silver doped β-alumina and in FIG. 6 for ½ mole % copper doped β-alumina. From FIGS. 5 and 6, when compared with FIG. 1, it can be seen that silver doped β-alumina and copper doped β-alumina are superior in response to sulphur dioxide concentration in that hysteresis is reduced. It is to be noted that FIG. 1 is plotted on a different scale to FIGS. 5 and 6.

It can be further seen that the silver doped β-alumina exhibits improved performance over the copper doped β-alumina at lower sulphur dioxide concentrations while copper exhibits improved performance at higher sulphur dioxide concentrations.

EXAMPLE 2

Figure 7:
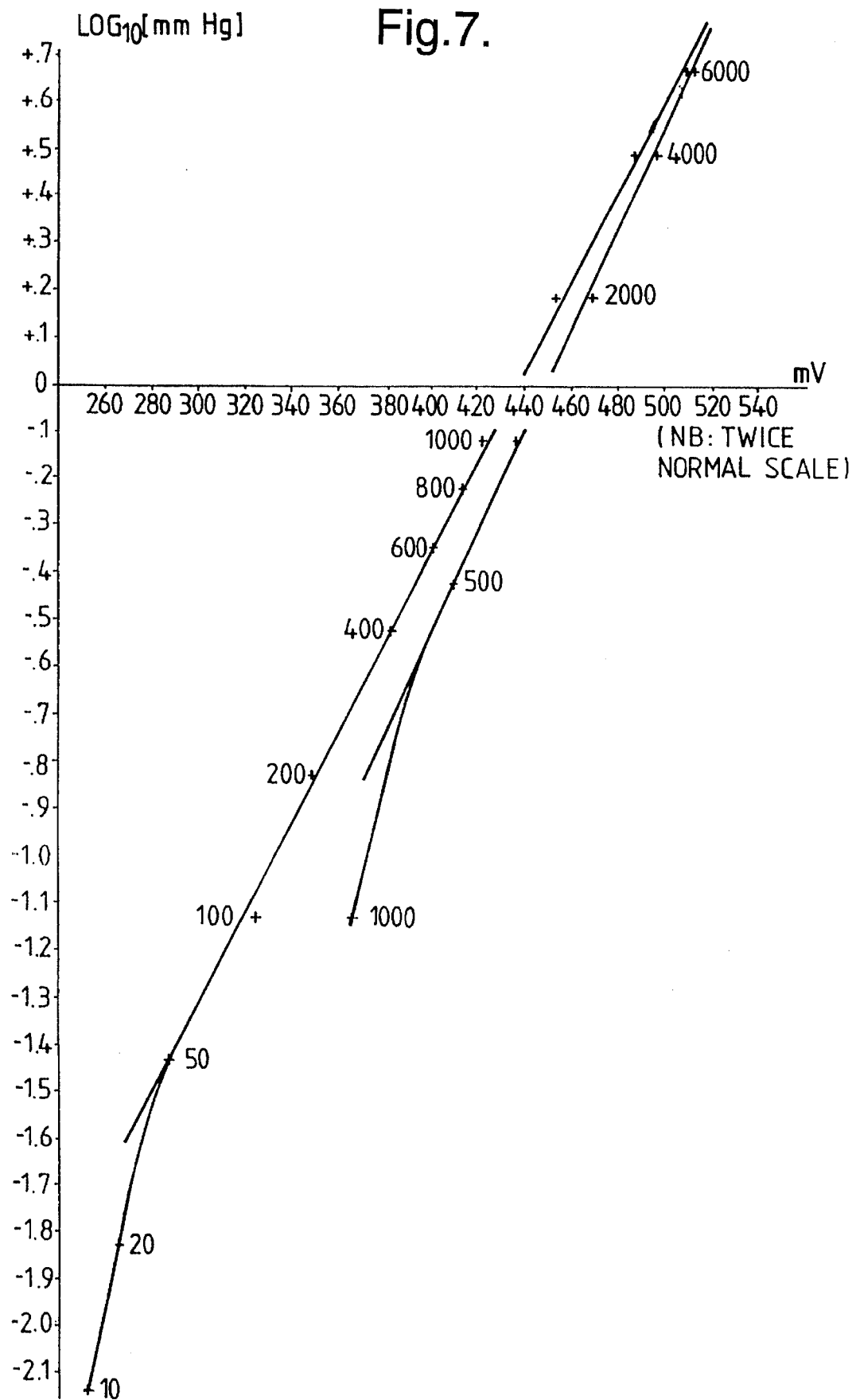
FIG. 7 is a Nernstian plot of sulphur dioxide response for 2 mole % copper doped β-alumina.
Figure 8:
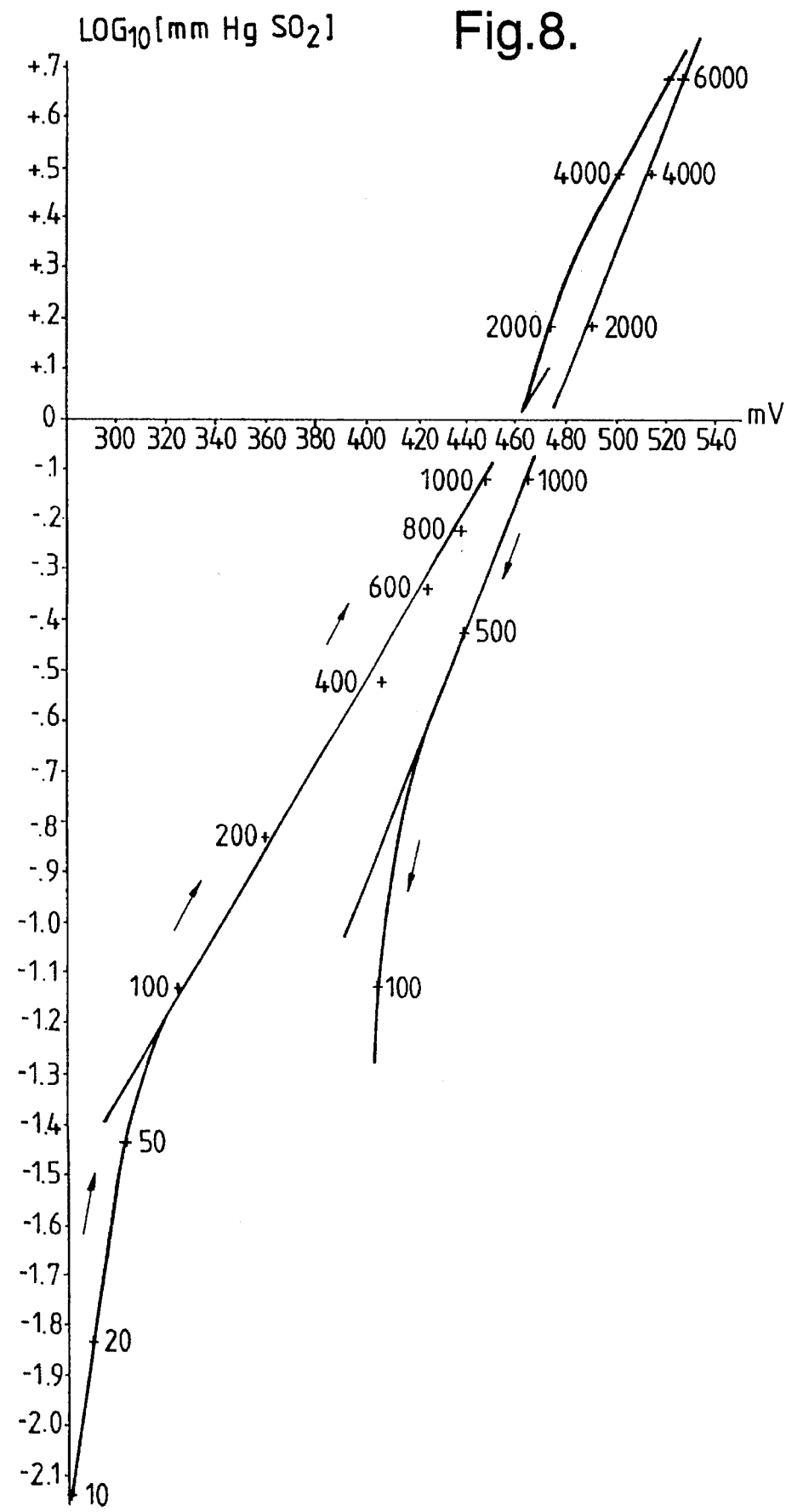
FIG. 8 is a Nernstian plot of sulphur dioxide response for 5 mole % copper doped β-alumina.

The experiment of Example 1 was repeated using β-alumina doped with 2 mole % and 5 mole % copper. The Nernstian plots of the results are given in FIGS. 7 and 8 respectively.

When these plots are compared with FIG. 6, it can be seen that for copper dopants, ½ mole % doped β-alumina provides superior results in terms of hysteresis and linear or Nernstian range.

EXAMPLE 3

To test the performance of the probes of the present invention under conditions approximate to those of practical application, two β-alumina samples were prepared. The first was undoped, the second doped with 2 mole % silver. The samples were then made up into prototype probes and installed into field trial sites. The undoped β-alumina probe was installed in the duct of a lead-zinc ore roaster and the 2% silver β-alumina probe in the duct of a pulverised coal electricity generating station. Both flue gases had a similar composition, both having typically 500–2000 ppm sulphur dioxide and 0–5% oxygen concentrations.

Figure 9A:
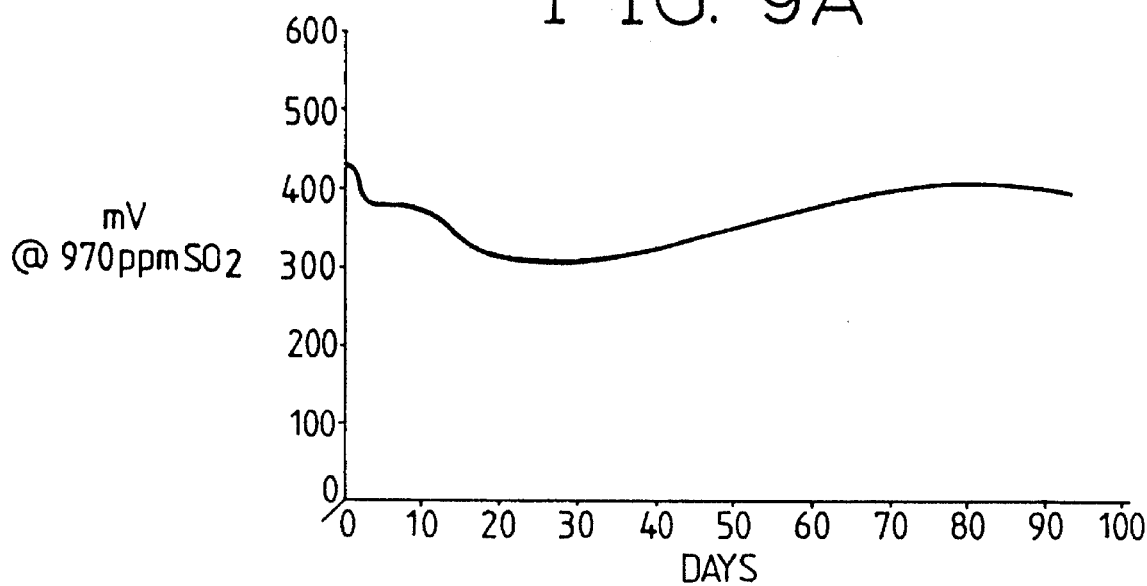
FIGS. 9a, 9b and 9c depict trends with time of response characteristics for undoped β-alumina.
Figure 9B:
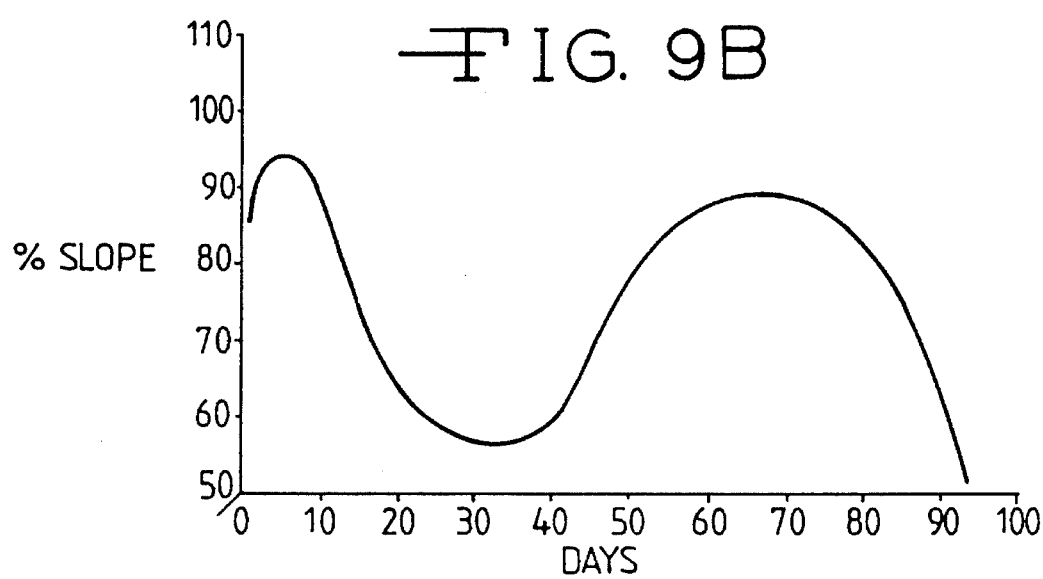
Figure 9C:
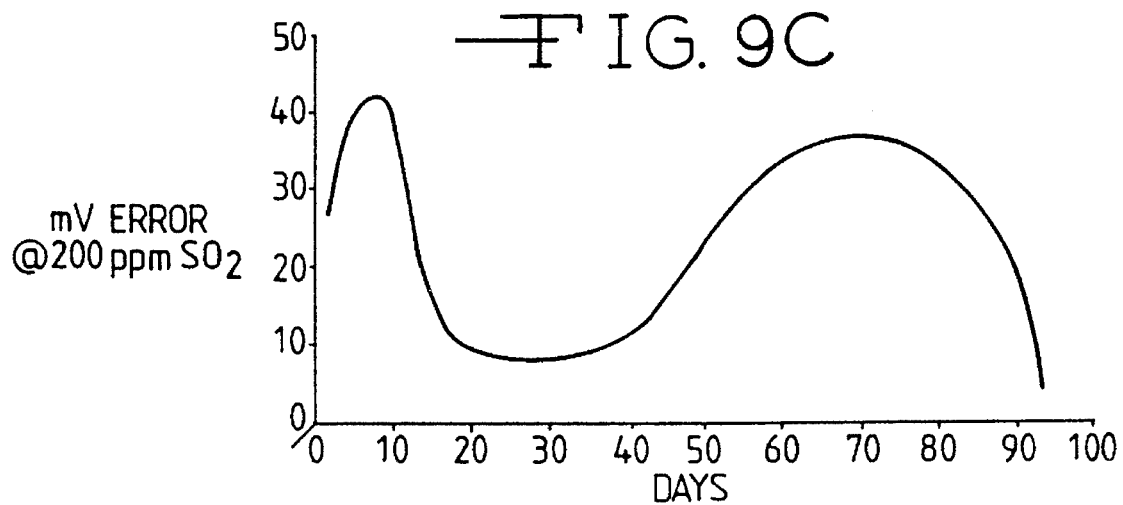
Figure 10A:
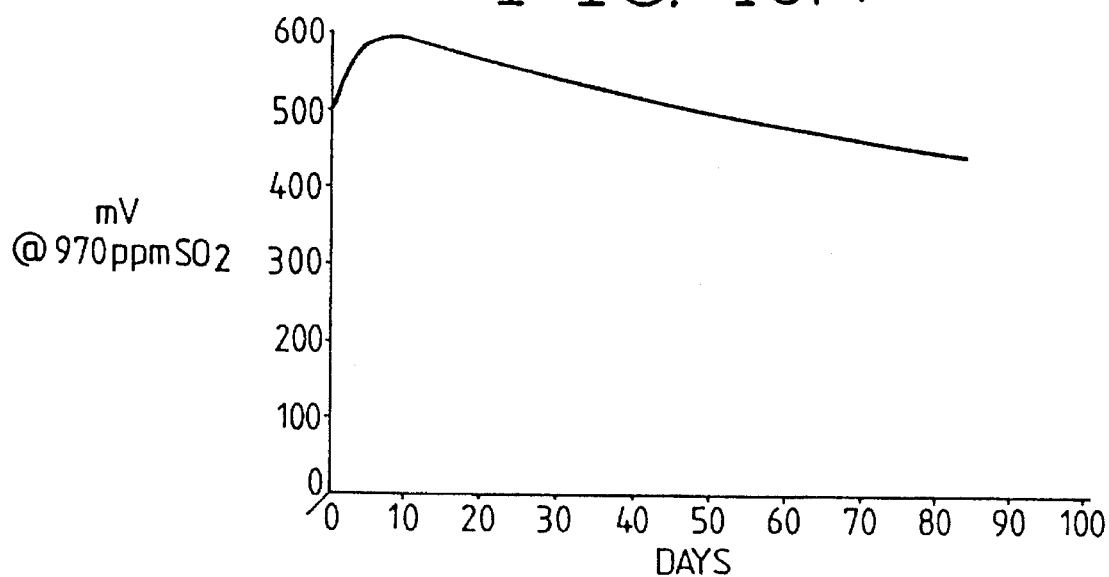
FIGS. 10a, 10b and 10c depict trends with time of response characteristics for 2 mole % silver doped β-alumina.
Figure 10B:
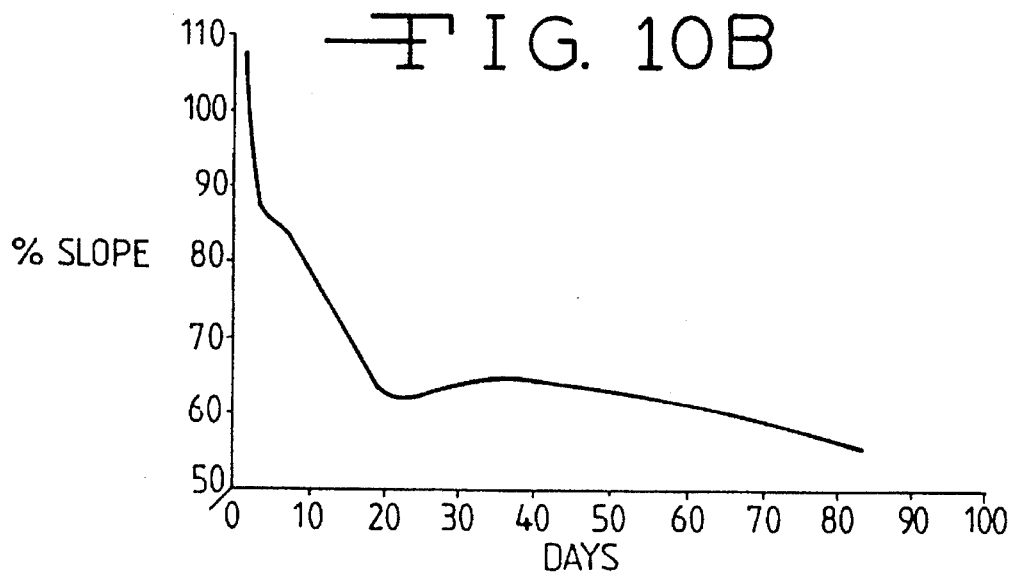
Figure 10C:
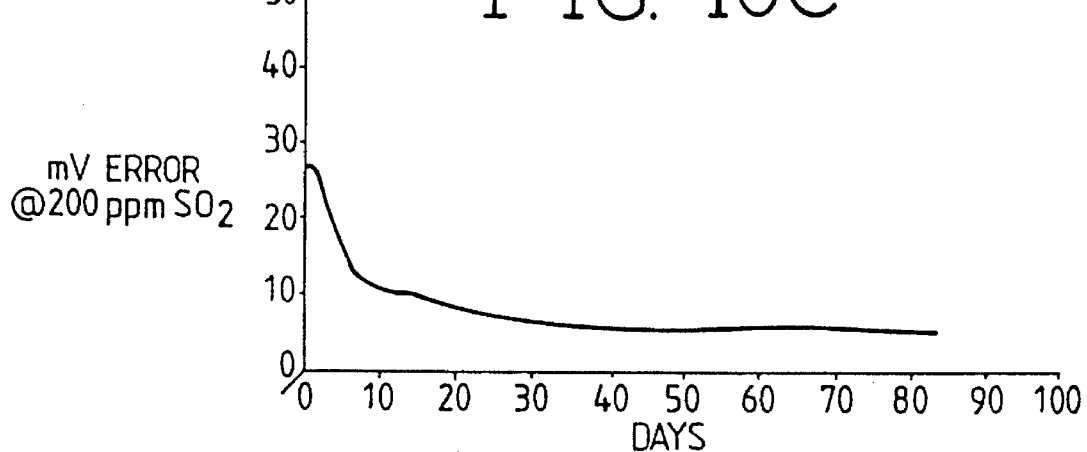

The trends with time of the response to 970 ppm sulphur dioxide (in air) test gas (a measure of zero offset drift), % slope and millivomits offset/hysteresis error at 200 ppm sulphur dioxide are shown in FIGS. 9 and 10 for the undoped β-alumina probe and for the 2% silver doped β-alumina probe respectively.

It can be see that the trends are smoother for the silver doped material and that this probe stabilises to a steady trend after a shorter period of running time.

EXAMPLE 4

To examine the mode by which the dopant is effecting the improvements in performance an AC impedance examination was carried out. The AC impedance spectroscopy technique enables the complex impedances of the cross-grain (bulk), grain boundary and electrode-electrolyte interface to be separated and examined individually. The method consists of measuring and analysing the complex impedances of the sample at a series of spot frequencies (in the present study from 5 Hz to 1 MHz). The cross-grain (bulk) wave is seen at the high frequency end of the range, the grain boundary wave at the mid-frequencies, and the electrode-electrolyte wave at the low frequency end. This order goes from left to right in the plots of FIGS. 12(a)–12(c) and 13(a). The measurements and data processing were carried out according to the methods of 'The Principles of Current Methods for the Study of Electrochemical Reactions' by B. B. Damaskin, McGraw-Hill, 1967 and in 'Impedance Spectroscopy' by J. R. Macdonald, John Wiley, 1987.

AC impedance plots were made first with undoped/β-alumina operated at 700° C. (the normal working temperature when used as a sulphur dioxide sensor). The test sample was arranged symmetrically with a porous platinum electrode on each face and exposed to the same gas mixture on each face for the purposes of these tests.

Figure 11:
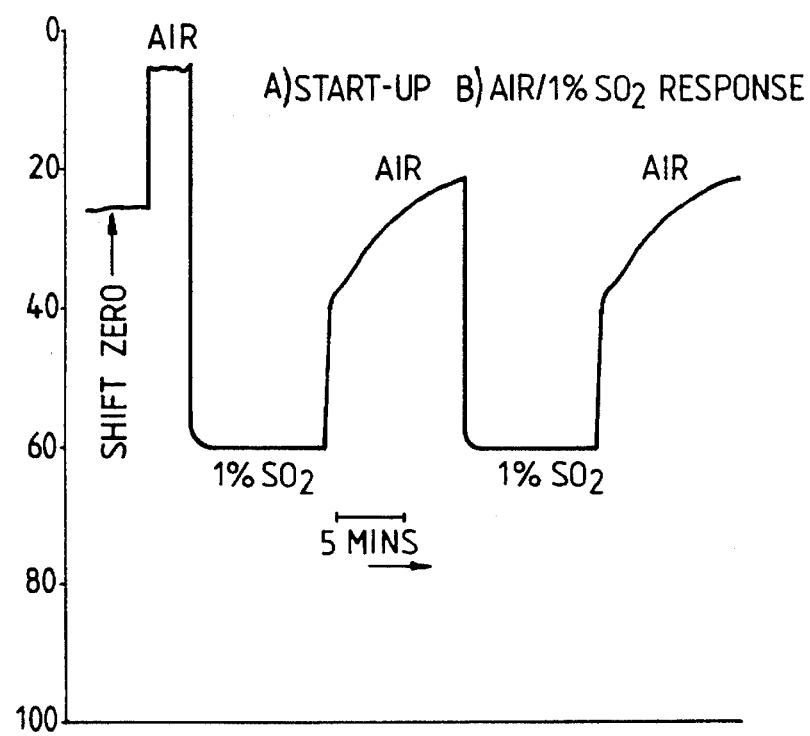
FIG. 11 is a plot of response of sensing system of 1% sulphur dioxide/0% sulphur dioxide (in air) step changes for undoped β-alumina.

The tests were conducted to establish what was happening during a gas step change going from a high sulphur dioxide concentration to a low concentration as it is here that the departure from theoretical response shows most clearly. This effect has already been illustrated in FIGS. 1 and 5 to 8 where the sub-theoretical response can be seen for decreasing sulphur dioxide concentrations. During a step change from 1% sulphur dioxide to 0% sulphur dioxide (in air) the sensor output is shown in the chart recording in FIG. 11 in which the response can be seen with a long sluggish 'tail'. This tail is due to the slow depolarization of the β-alumina.

Figure 12A:
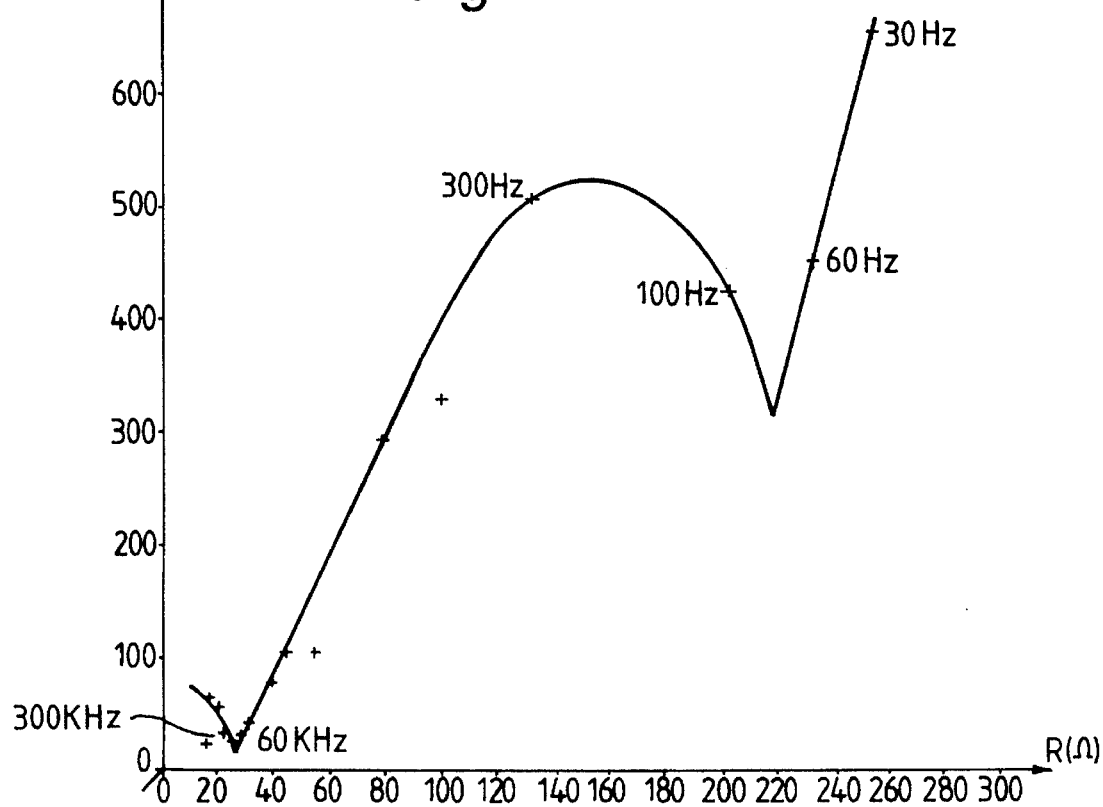
FIG. 12a is an a.c. impedance plot for undoped β-alumina in 1% sulphur dioxide.
Figure 12B:
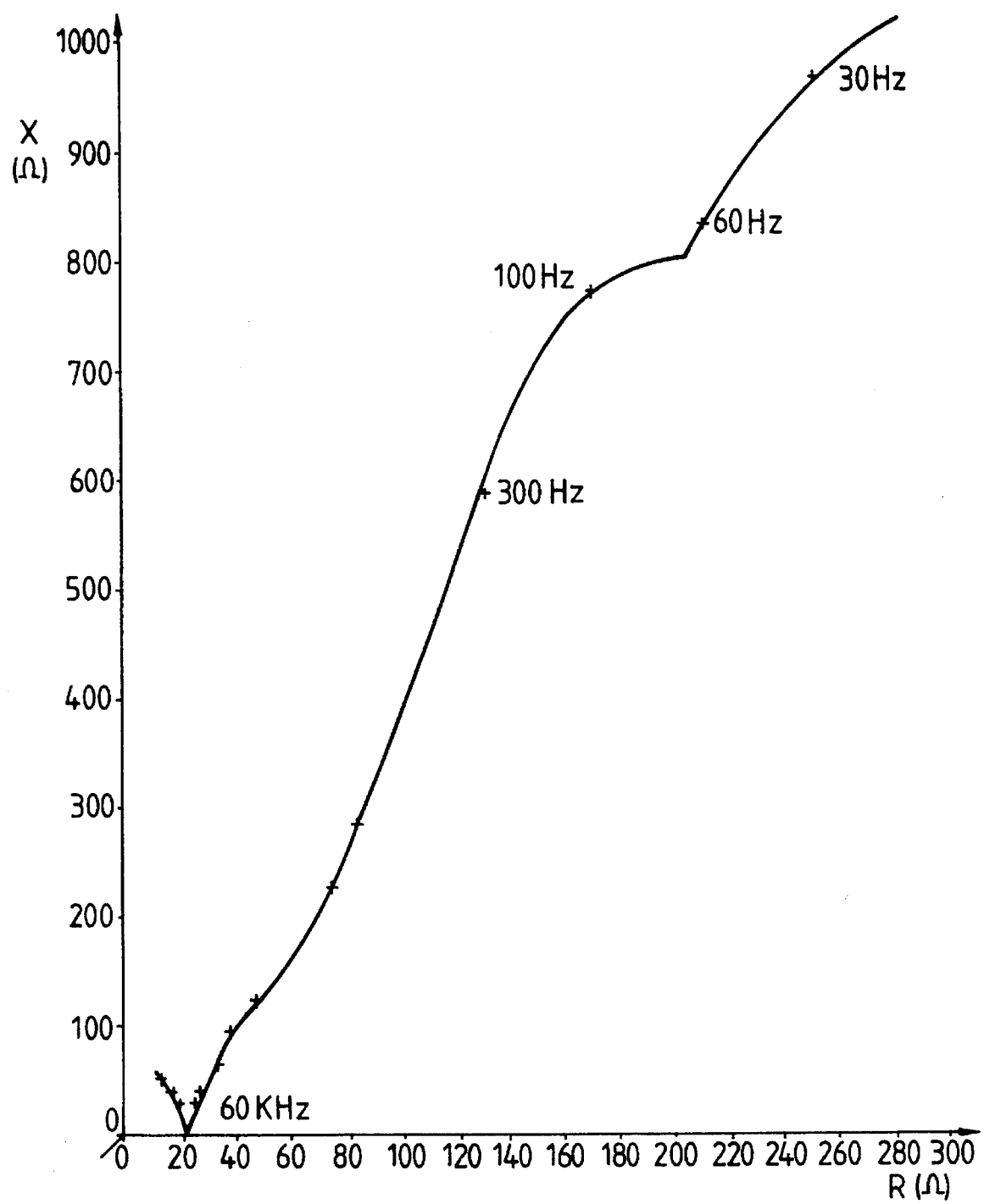
FIG. 12b is an a.c. impedance plot for undoped β-alumina, 2–4 mins after 1% to 0% sulphur dioxide step change.
Figure 12C:
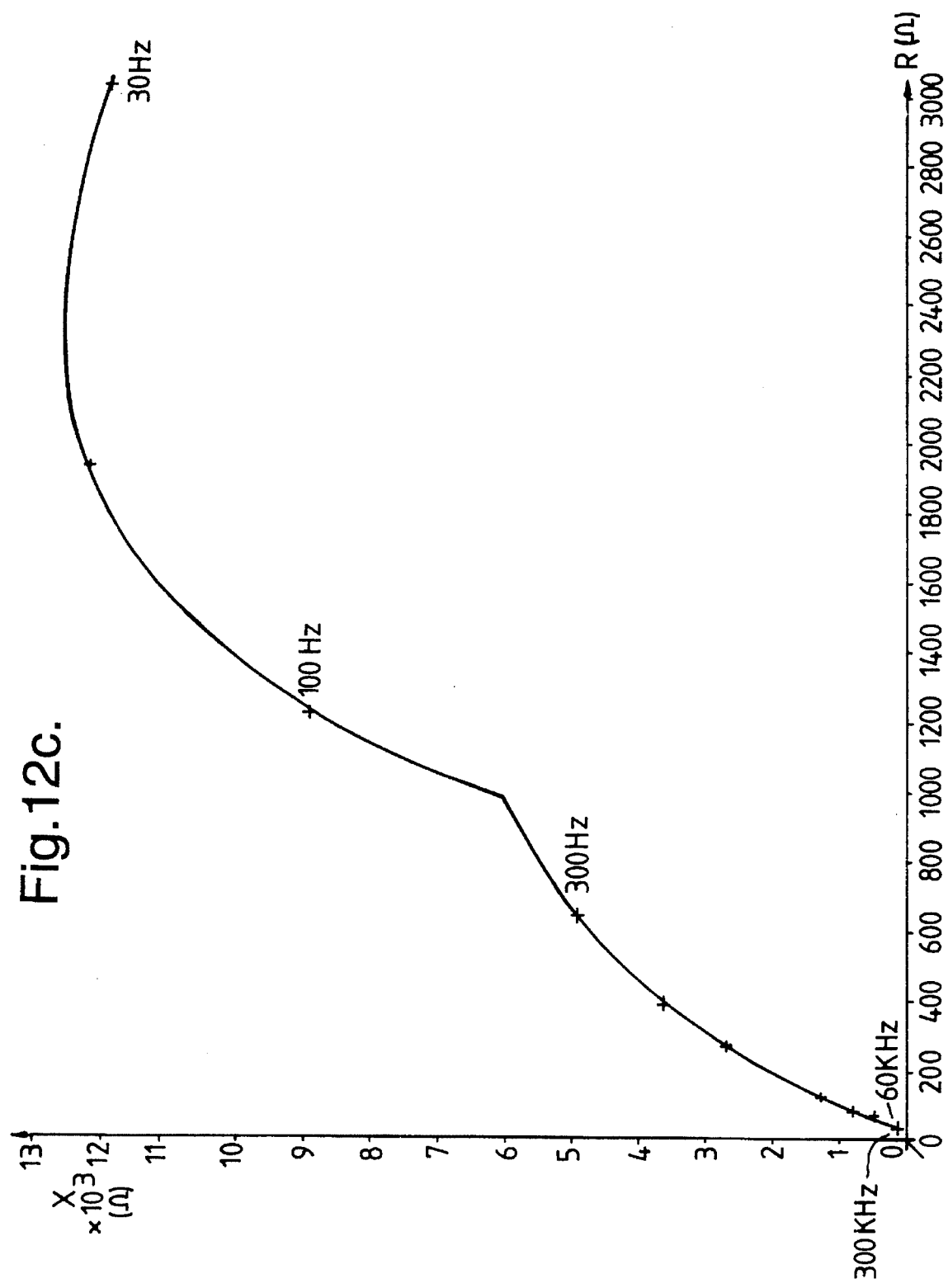
FIG. 12c is an a.c. impedance plot for undoped β-alumina in 0% sulphur dioxide.

For the undoped β-alumina sample the a.c. impedance plots were done for the sample fully stabilized and equilibrated in the presence of 1% sulphur dioxide in air (FIG. 12a) and in the presence of air i.e. 0% sulphur dioxide (FIG. 12c). The plot was then taken with each data point measured 2–4 minutes after the gas step change from 1% to 0% sulphur dioxide (FIG. 12b).

The significance of the results lie not in the intrinsic numerical values of the measured impedances but in the way in which they change during the step change. The plot 2–4 minutes after the step change (FIGS. 12a–12c) can be seen to have impedance values almost unchanged from 1% sulphur dioxide plot (FIG. 12a). (Note: FIG. 12c has axis scales an order of magnitude greater than FIGS. 12a & b).

The cross-grain (bulk) wave is the very small arc on the left. It does not change significantly between any of the plots and is therefore unlikely to be contributing to the polarization. This would be expected from the knowledge that the β-alumina crystals are super-ionic conductors i.e. they have very open planes within their crystal structure which allow very facile ion conduction.

However, it can be seen that both the grain boundary wave (the arc in the middle of the spectrum) and the electrode-electrolyte wave (the arc at the right of the plot) are both severely lagging during the step change. Hence the polarization of these components are both likely to be the main contributors to the observed deviations in electrochemical response.

Figure 13A:
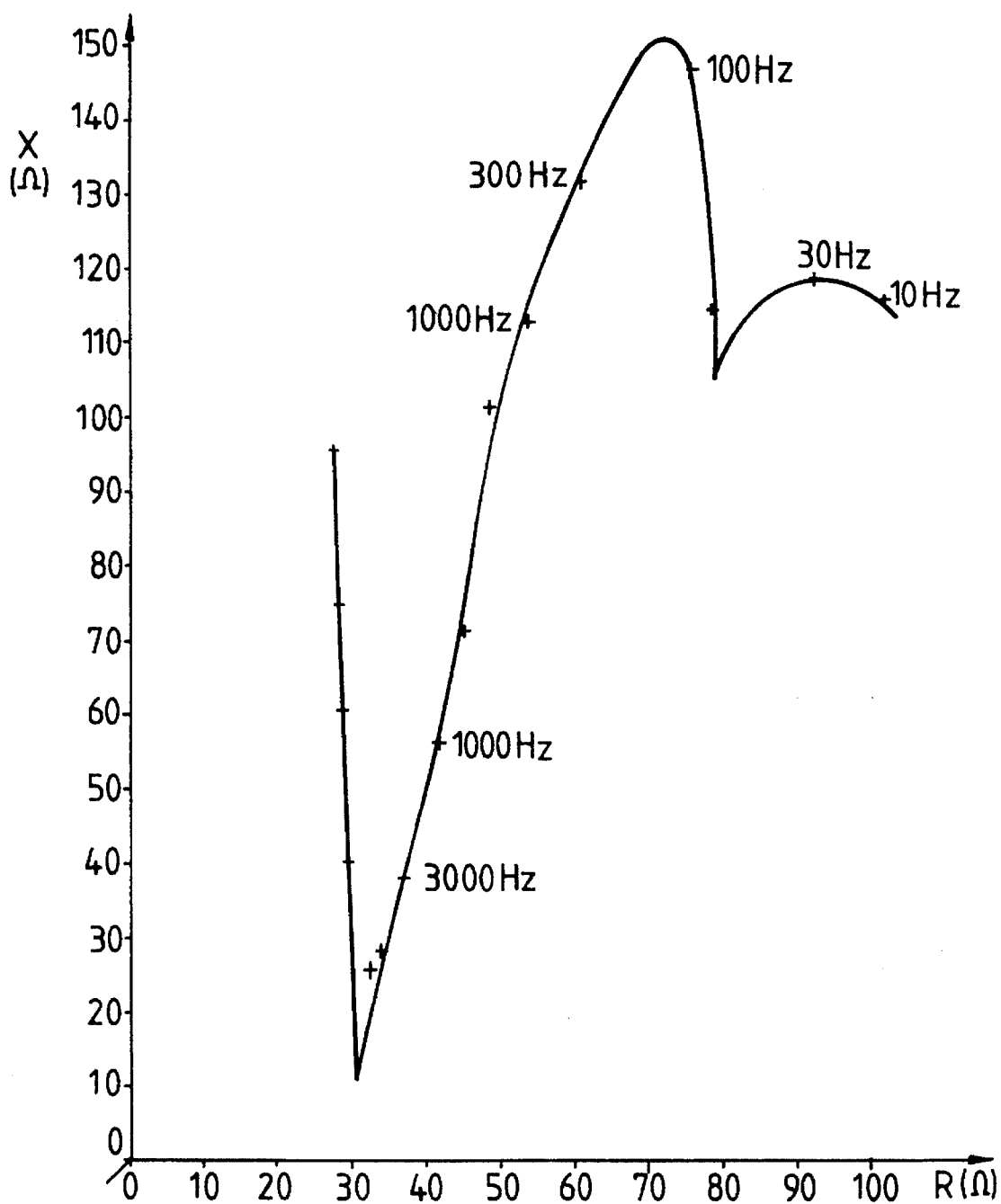
FIG. 13a is an a.c. impedance plot for 2 mole % silver doped β-alumina in 1% sulphur dioxide.
Figure 13B:
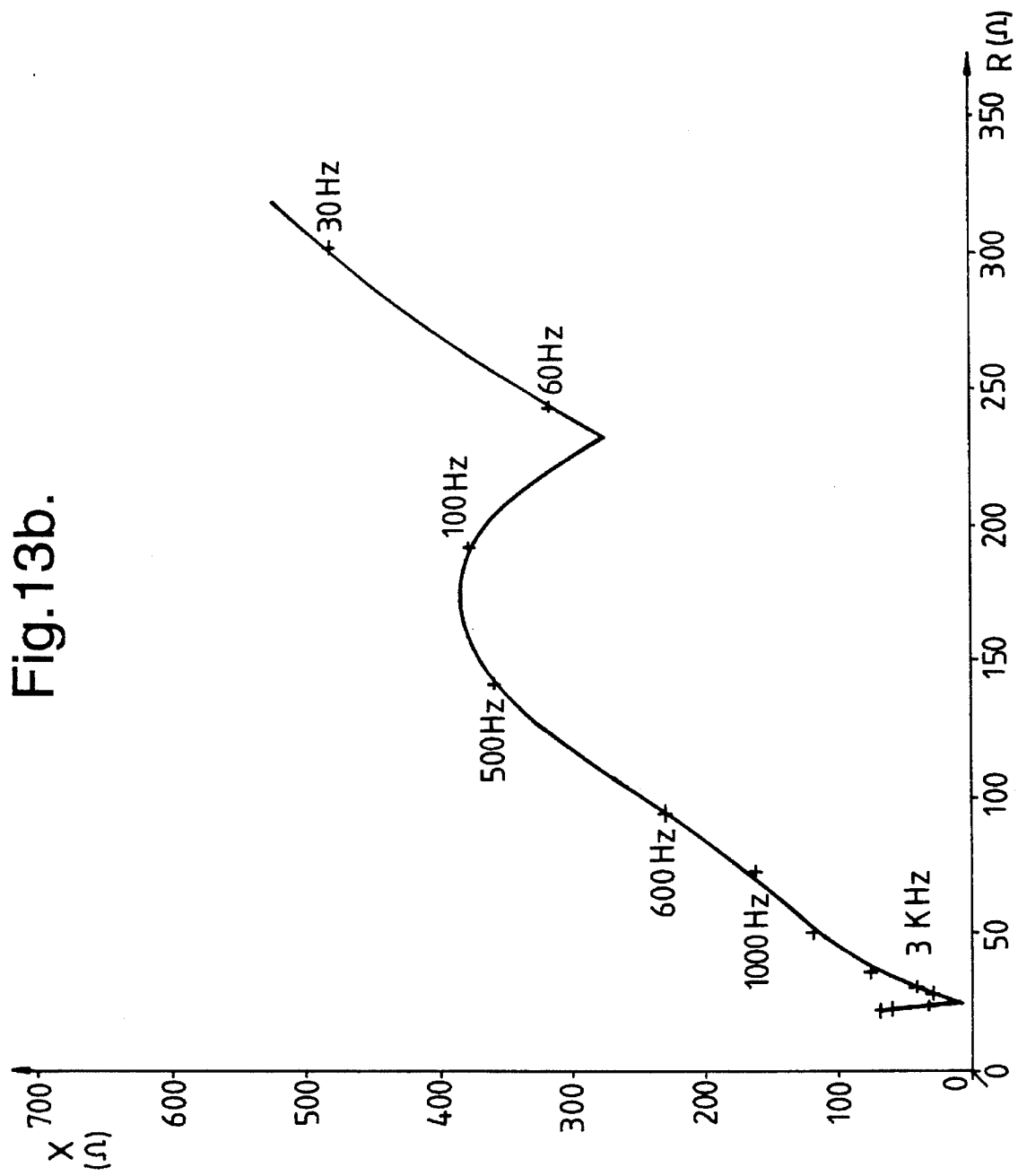
FIG. 13b is an a.c. impedance plot for 2 mole % silver doped β-alumina, 2–4 mins after 1% to 0% sulphur dioxide step change.
Figure 13C:
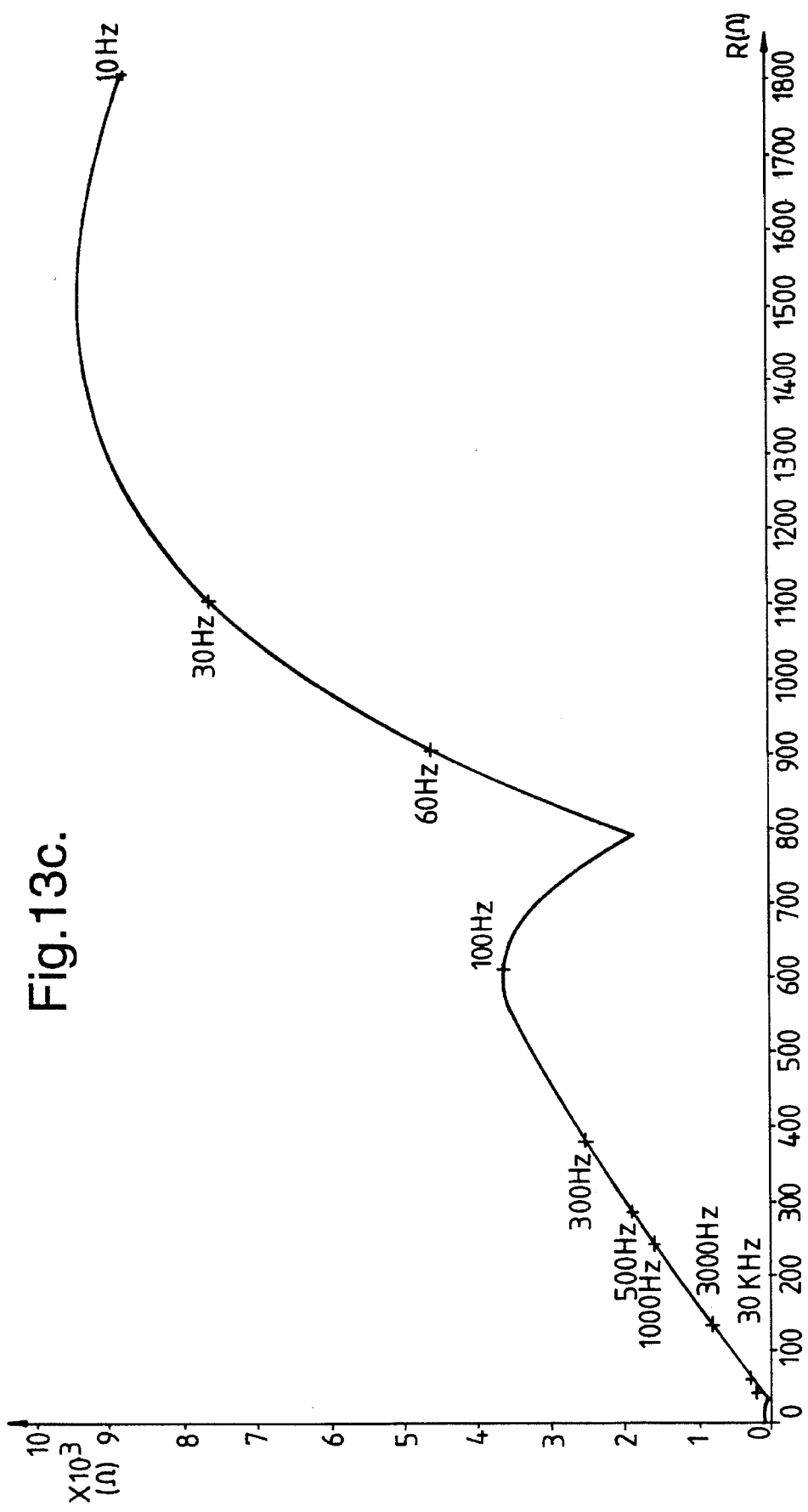
FIG. 13c is an a.c. impedance plot for 2 mole % silver doped β-alumina in 0% sulphur dioxide.
Figure 15B:
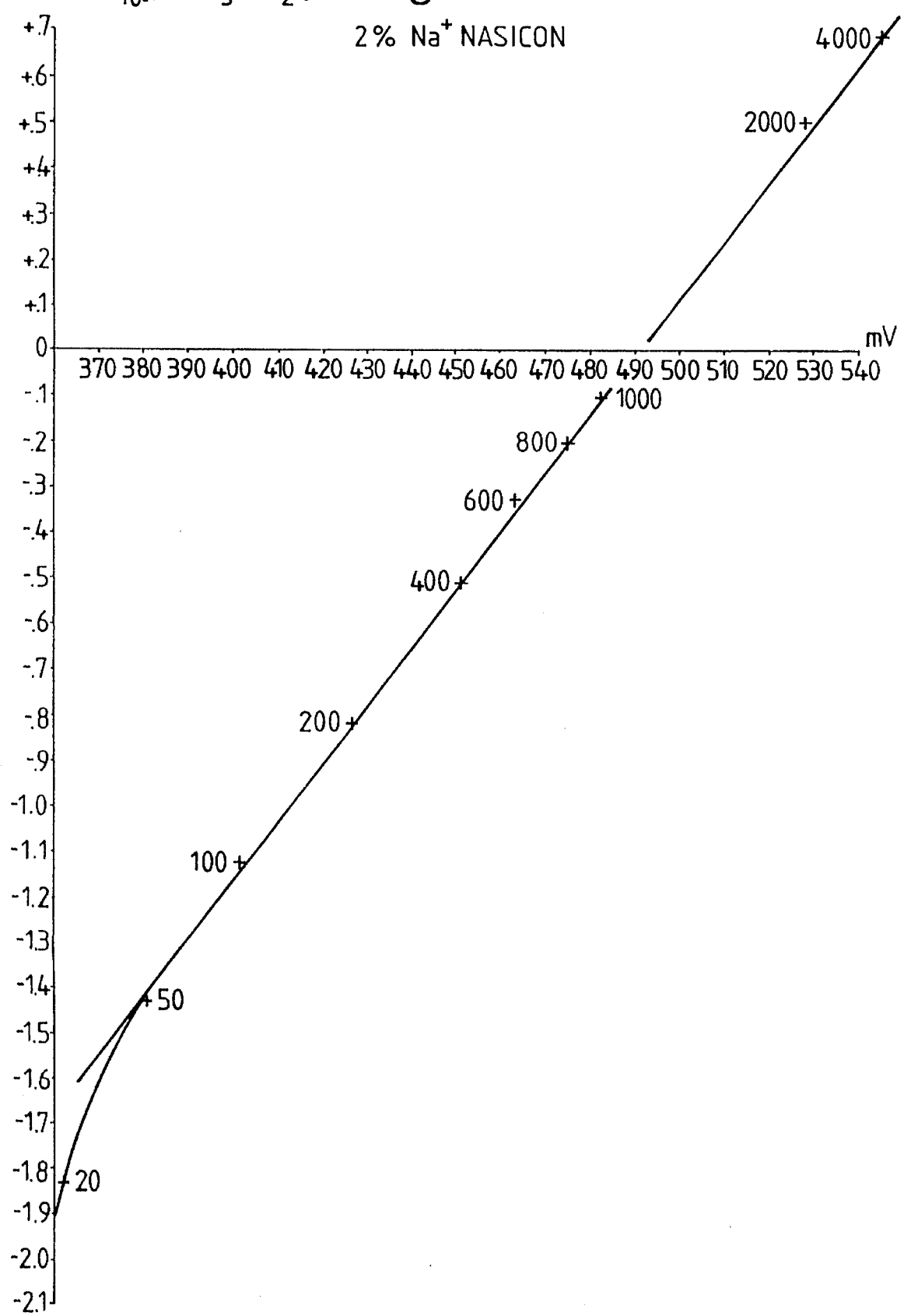
Figure 15D:
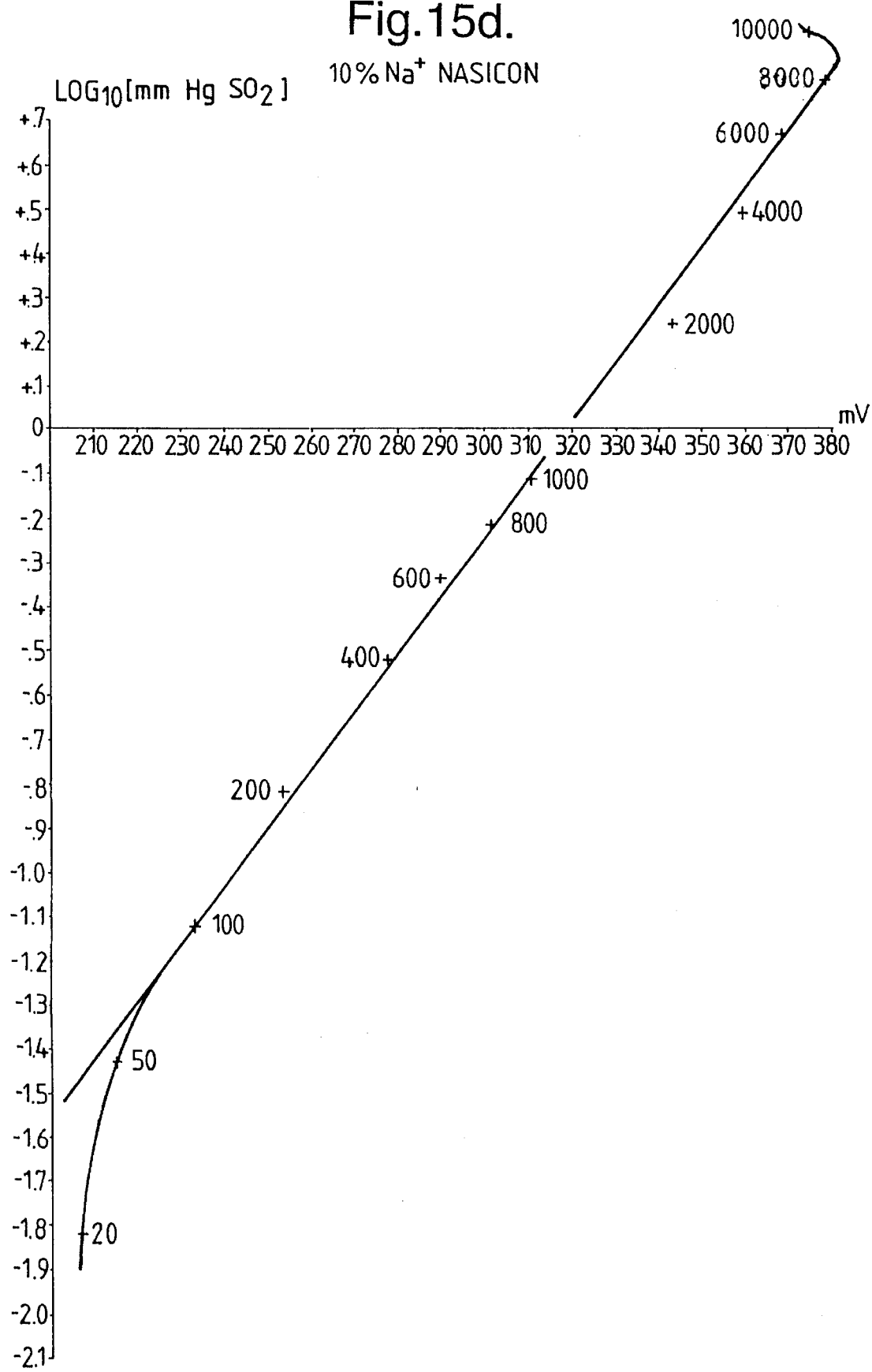

The same experiment was then performed on a sample of 2 mole % silver doped β-alumina. Again the a.c. impedance plots were made for equilibrium with 1% sulphur dioxide (FIG. 13a), and 0% sulphur dioxide (FIG. 13c) with the additional plot corresponding to 2–4 minutes following the step change from 1% to 0% sulphur dioxide (FIG. 13b).

It can be seen (after taking into account the different axis scales of the plots) that the shift in the grain boundary wave impedance and electrode-electrolyte wave impedances 2–4 minutes after the step change have moved significantly further towards the final 0% sulphur dioxide values compared with the undoped β-alumina. The effect is more pronounced for the grain boundary wave. Again the cross-grain (bulk) wave is unchanged throughout and is unlikely to be contributing to the polarization effects.

Therefore it is concluded that the dopant acts in improving the performance characteristics of the sulphur dioxide measurement by reduction of the polarization within the grain boundaries and at the electrode-electrolyte interface. Any dopant acting by this mechanism would also effect the same improvement in performance.

EXAMPLE 5

Tests were carried out in relation to various reference half cells. For comparison of the experimental results the response of the β-alumina sensing half cell (undoped β-alumina) using a reference system of 100 ppm sulphur dioxide in air in contact with a platinum electrode on the other side of the β-alumina disc is shown in FIG. 14.

This may be compared with the responses of undoped β-alumina in combination with NASICON with sodium ion excesses (mole %) of 1%, 2%, 5%, and 10% shown in FIGS. 15a, b, c, d. NASICON with no excess sodium ion also works (FIG. 16) although its reduced linear range indicates that the reference potential is such that the β-alumina is operating towards one end of its response range. All these tests were conducted with the reference exposed to air.

EXAMPLE 6

The NASICON material $Na_3YZr_3(PO_4)_6$ (*Solid State Ionics*, 58, 327, 1992) in which $yttrium^{3+}$ substitution has been used to adjust the sodium ion concentration has also been prepared and tested. The effectiveness of this material as a reference is shown by the sharp response during step changes between 1% and 0% sulphur dioxide in air when combined with a disc of 2 mole % silver doped β-alumina (FIG. 17). Again the reference used was exposed to air.

EXAMPLE 7

An alternative candidate for reference material is the (α+β) phase β-alumina. FIG. 18 shows the Nernstian plot of undoped β-alumina when combined with this reference (exposed to air). The example illustrated is operating towards the end of the β-alumina operating range and hence departs from theory at one end. This material is not so useful as the NASICON-based reference as it is more difficult to manufacture with reproducible phase composition.

While the description of the sensor has been directed to sensors for measuring sulphur dioxide, it will be appreciated that the apparatus and process of the present inventions can be used to detect other oxides of sulphur, in particular, sulphur trioxide.

It will further be appreciated that while the description has been directed to the detection of oxides of sulphur, in particular of sulphur dioxides, the apparatus and method of the present invention can be used to detect other gaseous oxides.

I claim:

1. A sensor for measuring a sulphur oxide in gas, comprising a sensing element directly exposed to the gas to be measured and electrode means for use in measuring an electrochemically developed potential, characterized in that the sensing element comprises an electrolyte of doped β-alumina or doped NASICON, the dopant being chosen to improve polarization effects in the electrolyte thereby reducing hysteresis in the presence of sulphur dioxide.

2. A sensor according to claim 1, wherein the dopant is selected to increase conductivity at grain boundaries in the sensing element, thereby to increase the rate of grain boundary depolarization.

3. A sensor according to claim 1, wherein the dopant is selected to increase conductivity at the interface between the sensing element and the electrode means, thereby to increase the rate of interfacial depolarization.

4. A sensor according to claim 1, wherein the sensing element comprises an electrolyte of β-alumina or NASICON doped with a first dopant selected to increase conductivity at grain boundaries in the sensing element, thereby to increase the rate of grain boundary depolarization and doped with a second dopant selected to increase conductivity at the interface between the sensing element and the electrode means, thereby to increase the rate of interfacial depolarization.

5. A sensor according to claim 1, wherein the β-alumina or NASICON is doped with silver, copper, nickel, uranium, chromium, manganese, cobalt, vanadium, cerium, palladium, iron, zinc, tin, mercury, cadmium, europium or rhodium.

6. A sensor according to claim 5, wherein the or each dopant is present in an amount of from 0.1 to 10 mol %.

7. A sensor according to claim 1, wherein the sensor additionally comprises a reference element, such that the measured potential directly related to the sulphur oxide level for a known oxygen level.

8. A sensor according to claim 7, wherein the reference element comprises a solid state electrolyte.

9. A sensor according to claim 8, wherein the electrolyte is NASICON having a selected sodium activity.

10. A sensor according to claim 8 or 9, wherein the electrolyte is doped NASICON.

11. A sensor according to claim 10, wherein the NASICON is doped with sodium.

12. A sensor according to claim 11, wherein the sodium is present in an amount of 33 mol % or less.

13. A sensor according to claim 8, wherein the electrolyte is (α+β) alumina.

14. A sensor according to claim 1, wherein the electrode means comprise a layer of platinum or perovskite-lanthanum nickelate.

15. A sensor according to claim 1 and responsive to sulphur dioxide.

16. A method of measuring sulphur dioxide in boiler flue gases, comprising the steps of exposing the flue gases to the sensing element of a sensor according to claim 1, and measuring the electrochemically developed potential.

17. A method according to claim 16, wherein the boiler flue gases are exposed to the sensing electrolyte without chilling.

18. A sulphur oxide sensor comprising a solid state sensing electrolyte directly exposed to and responsive to a sulphur oxide and to oxygen and a solid state reference electrolyte in electrochemical association with the sensing electrolyte such that the electrochemical response of the sensor is representative of the sulphur oxide level for a known level of oxygen, the reference electrolyte being selected from the group consisting of NASICON, doped NASICON, mixed phase alumina and doped alumina.

19. A probe for measuring a sulphur oxide in gas comprising a sensor according to claim 7 or claim 18 and an oxygen compensator associated with the sensing element and the reference electrolyte such that a measure of the sulphur oxide level is obtained which is independent of the oxygen level in the gas.

20. A probe according to claim 19, characterised in that the oxygen compensator comprises a zirconia oxygen sensor.

21. A sulphur oxide probe comprising a first sensing electrolyte responsive to the sulphur oxide and oxygen and a second sensing electrolyte in electrochemical association with the first sensing electrolyte and responsive to oxygen, wherein the first and second sensing electrolytes respond substantially equally to oxygen so that the overall response of the probe is indicative of the sulphur oxide level substantially independently of oxygen level.

22. A sensor for measuring gaseous oxides comprising a sensing element directly exposed to the gas to be measured and electrode means for use in measuring an electrochemically developed potential, characterized in that the sensing element comprises an electrolyte of doped β-alumina or doped NASICON, the dopant being chosen to improve polarization effects in the electrolyte thereby reducing hysteresis in the presence of the gaseous oxides.

23. A method of measuring a sulphur oxide in gas, comprising the steps of directly exposing to the gas a sensing electrolyte of doped β-alumina or doped NASICON and detecting an electrochemically developed potential, the dopant being chosen to improve polarization effects in the electrolyte thereby reducing hysteresis in the presence of sulphur dioxide.

24. A method according to claim 23, wherein the dopant is selected to increase conductivity at grain boundaries in the sensing element, thereby to increase the rate of grain boundary depolarization.

25. A method according to claim 23, wherein the dopant is selected to increase conductivity at the interface between the sensing element and the electrode means, thereby to increase the rate of interfacial depolarization.

26. A method according to claim 23, wherein the sensing element comprises an electrolyte of β-alumina or NASICON doped with a first dopant selected to increase conductivity at grain boundaries in the sensing element, thereby to increase the rate of grain boundary depolarization and doped with a second dopant selected to increase conductivity at the interface between the sensing element and the electrode means, thereby to increase the rate of interfacial depolarization.

27. A method according to claim 23, wherein the β-alumina or NASICON is doped with silver, copper, nickel, uranium, chromium, manganese, cobalt, vanadium, cerium, palladium, iron, zinc, tin, mercury, cadmium, europium or rhodium.

28. A method according to any one of claims 23 to 27, for measuring sulphur dioxide in boiler flue gases, wherein the boiler flue gases are exposed to the sensing electrolyte without chilling.

* * * * *